United States Patent
Trieu

(10) Patent No.: US 8,133,279 B2
(45) Date of Patent: Mar. 13, 2012

(54) METHODS FOR TREATING AN ANNULUS DEFECT OF AN INTERVERTEBRAL DISC

(75) Inventor: Hai H. Trieu, Cordova, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 203 days.

(21) Appl. No.: 11/621,173

(22) Filed: Jan. 9, 2007

(65) Prior Publication Data
US 2007/0255285 A1    Nov. 1, 2007

Related U.S. Application Data

(63) Continuation-in-part of application No. 11/412,272, filed on Apr. 27, 2006, now abandoned.

(51) Int. Cl.
*A61F 2/44*    (2006.01)
(52) U.S. Cl. .................. 623/17.11; 623/17.12
(58) Field of Classification Search .... 623/17.11–17.16; 606/86, 246, 279
See application file for complete search history.

(56) References Cited

U.S. PATENT DOCUMENTS

| | | |
|---|---|---|
| 3,875,595 A | 4/1975 | Froning |
| 4,772,287 A | 9/1988 | Ray et al. |
| 4,863,477 A | 9/1989 | Monson |
| 4,904,260 A | 2/1990 | Ray et al. |
| 5,047,055 A | 9/1991 | Bao et al. |
| 5,146,933 A | 9/1992 | Boyd |
| 5,171,280 A | 12/1992 | Baumgartner |
| 5,192,326 A | 3/1993 | Bao et al. |
| 5,331,975 A | 7/1994 | Bonutti |
| 5,342,298 A | 8/1994 | Michaels et al. |
| 5,344,459 A | 9/1994 | Swartz |
| 5,549,679 A | 8/1996 | Kuslich |
| 5,562,614 A | 10/1996 | O'Donnell |
| 5,562,736 A | 10/1996 | Ray et al. |
| 5,571,189 A | 11/1996 | Kuslich |
| 5,645,597 A | 7/1997 | Krapiva |
| 5,705,780 A | 1/1998 | Bao |
| 5,755,797 A | 5/1998 | Baumgartner |
| 5,824,093 A | 10/1998 | Ray et al. |
| 5,888,220 A | 3/1999 | Felt et al. |

(Continued)

FOREIGN PATENT DOCUMENTS
WO        2003011155 A2    2/2003
(Continued)

OTHER PUBLICATIONS

U.S. Appl. No. 11/412,272, filed Apr. 27, 2006.
(Continued)

*Primary Examiner* — Thomas C. Barrett
*Assistant Examiner* — Andrew Yang

(57) ABSTRACT

A system for treating an annular defect of an intervertebral disc is provided. The system comprises a cannula for accessing a nucleus pulposus of the intervertebral disc, an expandable spacing device, and a material delivery instrument. The expandable spacing device has a first deflated position and a second inflated position. The spacing device is sized to pass through the cannula when in the first deflated position and the spacing device has a predetermined shape in the second inflated position. The material delivery instrument is adapted to inflate the spacing device from the first deflated position to the second inflated position by injecting a biocompatible material into the spacing device. In another aspect, a method of treating at least one annular defect of an intervertebral disc is provided.

9 Claims, 17 Drawing Sheets

U.S. PATENT DOCUMENTS

| | | | |
|---|---|---|---|
| 5,919,235 | A | 7/1999 | Husson et al. |
| 5,928,284 | A | 7/1999 | Mehdizadeh |
| 6,022,376 | A | 2/2000 | Assell |
| 6,132,465 | A | 10/2000 | Ray et al. |
| 6,140,452 | A | 10/2000 | Felt et al. |
| 6,165,218 | A | 12/2000 | Husson et al. |
| 6,187,048 | B1 | 2/2001 | Milner et al. |
| 6,231,609 | B1 | 5/2001 | Mehdizadeh |
| 6,248,131 | B1 | 6/2001 | Felt et al. |
| 6,264,695 | B1 | 7/2001 | Stoy |
| 6,375,682 | B1 | 4/2002 | Fleischmann et al. |
| 6,402,750 | B1 | 6/2002 | Atkinson et al. |
| 6,419,704 | B1 | 7/2002 | Ferree |
| 6,425,919 | B1 | 7/2002 | Lambrecht |
| 6,482,234 | B1 | 11/2002 | Weber et al. |
| 6,482,235 | B1 | 11/2002 | Lambrecht et al. |
| 6,508,839 | B1 | 1/2003 | Lambrecht et al. |
| 6,533,817 | B1 | 3/2003 | Norton et al. |
| 6,607,544 | B1 | 8/2003 | Boucher et al. |
| 6,645,248 | B2 | 11/2003 | Casutt |
| 6,692,495 | B1 | 2/2004 | Zacouto |
| 6,692,528 | B2 | 2/2004 | Ward et al. |
| 6,712,853 | B2 | 3/2004 | Kuslich |
| 6,726,721 | B2 | 4/2004 | Stoy et al. |
| 6,733,533 | B1 | 5/2004 | Lozier |
| 6,764,514 | B1 | 7/2004 | Li et al. |
| 6,783,546 | B2 | 8/2004 | Zucherman et al. |
| 6,835,205 | B2 | 12/2004 | Atkinson et al. |
| 6,849,092 | B2 | 2/2005 | Van Dyke et al. |
| 6,893,465 | B2 | 5/2005 | Huang |
| 6,958,077 | B2 | 10/2005 | Suddaby |
| 7,001,431 | B2 | 2/2006 | Bao et al. |
| 7,094,258 | B2 | 8/2006 | Lambrecht et al. |
| 2001/0004710 | A1 | 6/2001 | Felt et al. |
| 2001/0049527 | A1 | 12/2001 | Cragg |
| 2002/0016583 | A1 | 2/2002 | Cragg |
| 2002/0026195 | A1 | 2/2002 | Layne et al. |
| 2002/0049498 | A1 | 4/2002 | Yuksel et al. |
| 2002/0059001 | A1 | 5/2002 | Yuksel et al. |
| 2002/0082608 | A1 | 6/2002 | Reiley et al. |
| 2002/0107573 | A1 | 8/2002 | Steinberg |
| 2002/0177866 | A1 | 11/2002 | Weikel et al. |
| 2003/0028251 | A1 | 2/2003 | Mathews |
| 2003/0040800 | A1 | 2/2003 | Li et al. |
| 2003/0074075 | A1 | 4/2003 | Thomas, Jr. et al. |
| 2003/0074076 | A1 | 4/2003 | Ferree et al. |
| 2003/0083642 | A1 | 5/2003 | Boyd et al. |
| 2003/0153976 | A1 | 8/2003 | Cauthen, III et al. |
| 2003/0195628 | A1 * | 10/2003 | Bao et al. .................. 623/17.12 |
| 2004/0024463 | A1 | 2/2004 | Thomas, Jr. et al. |
| 2004/0030392 | A1 | 2/2004 | Lambrecht et al. |
| 2004/0073308 | A1 | 4/2004 | Kuslich et al. |
| 2004/0093087 | A1 | 5/2004 | Ferree et al. |
| 2004/0097980 | A1 * | 5/2004 | Ferree ........................... 606/151 |
| 2004/0102774 | A1 | 5/2004 | Trieu |
| 2004/0133280 | A1 | 7/2004 | Trieu |
| 2004/0186471 | A1 | 9/2004 | Trieu |
| 2004/0186576 | A1 | 9/2004 | Biscup et al. |
| 2004/0210297 | A1 | 10/2004 | Lin et al. |
| 2004/0210315 | A1 | 10/2004 | Li et al. |
| 2004/0215342 | A1 | 10/2004 | Suddaby |
| 2005/0055094 | A1 | 3/2005 | Kuslich |
| 2005/0060036 | A1 | 3/2005 | Schultz et al. |
| 2005/0090901 | A1 | 4/2005 | Studer |
| 2005/0119662 | A1 | 6/2005 | Reiley et al. |
| 2005/0171611 | A1 | 8/2005 | Stoy et al. |
| 2005/0197702 | A1 | 9/2005 | Coppes et al. |
| 2005/0203206 | A1 | 9/2005 | Trieu |
| 2005/0209601 | A1 | 9/2005 | Bowman et al. |
| 2005/0209602 | A1 | 9/2005 | Bowman et al. |
| 2005/0240269 | A1 * | 10/2005 | Lambrecht et al. ........ 623/17.13 |
| 2006/0253132 | A1 * | 11/2006 | Evans et al. .................... 606/151 |
| 2007/0005140 | A1 | 1/2007 | Kim et al. |
| 2007/0043374 | A1 * | 2/2007 | Evans ............................. 606/86 |

FOREIGN PATENT DOCUMENTS

| | | |
|---|---|---|
| WO | WO2004073563 A2 | 9/2004 |
| WO | 2004093729 A2 | 11/2004 |

OTHER PUBLICATIONS

International Search Report and Written Opinion, Jul. 30, 2008.
Office Action mailed Jan. 30, 2009 in U.S. Appl. No. 11/412,558, filed Apr. 27, 2006.

* cited by examiner

METHODS FOR TREATING AN ANNULUS DEFECT OF AN INTERVERTEBRAL DISC

CROSS REFERENCE

This application is a continuation-in-part of co-pending application Ser. No. 11/412,272, entitled "Devices, Apparatus, and Methods for Bilateral Approach to Disc Augmentation," filed Apr. 27, 2006, which is herein incorporated by reference in its entirety.

BACKGROUND

Within the spine, the intervertebral disc functions to stabilize and distribute forces between vertebral bodies. The intervertebral disc comprises a nucleus pulposus which is surrounded and confined by the annulus fibrosis. Intervertebral discs are prone to injury and degeneration. For example, herniated discs typically occur when normal wear, or exceptional strain, causes a disc to rupture. Degenerative disc disease typically results from the normal aging process, in which the tissue gradually loses its natural water and elasticity, causing the degenerated disc to shrink and possibly rupture.

Intervertebral disc injuries and degeneration are frequently treated by replacing or augmenting the existing disc material. Current methods and instrumentation used for treating the disc require a relatively large hole to be cut in the disc annulus to allow introduction of the implant. After the implantation, the large hole in the annulus must be plugged, sewn closed, or other wise blocked to avoid allowing the implant to be expelled from the disc. Besides weakening the annular tissue, creation of the large opening and the subsequent repair adds surgical time and cost. A need exists for devices, instrumentation, and methods for implanting an intervertebral implant using minimally invasive surgical techniques.

SUMMARY

In one embodiment, a method for treating at least one defect in an annulus of an intervertebral disc is provided. The method includes providing a spacing device having a first deflated position and a second inflated position, wherein the spacing device has a predetermined shape in the second inflated position. The method also includes creating an opening to access the intervertebral disc, inserting the spacing device while in the deflated position through the first opening and into the nucleus pulposus of the intervertebral disc adjacent the at least one defect of the annulus, and injecting a biomaterial into the spacing device to expand the spacing device from the first deflated position to the second inflated position. The expansion of the spacing device occurs without removing a portion of the nucleus pulposus.

In another embodiment, a system for treating an annular defect of an intervertebral disc is provided. The system comprises a cannula for accessing a nucleus pulposus of the intervertebral disc, an expandable spacing device, and a material delivery instrument. The expandable spacing device has a first deflated position and a second inflated position. The spacing device is sized to pass through the cannula when in the first deflated position and the spacing device has a predetermined shape in the second inflated position. The material delivery instrument is adapted to inflate the spacing device from the first deflated position to the second inflated position by injecting a biocompatible material into the spacing device.

Additional embodiments are included in the attached drawings and the description provided below.

DETAILED DESCRIPTION

Figure 1:
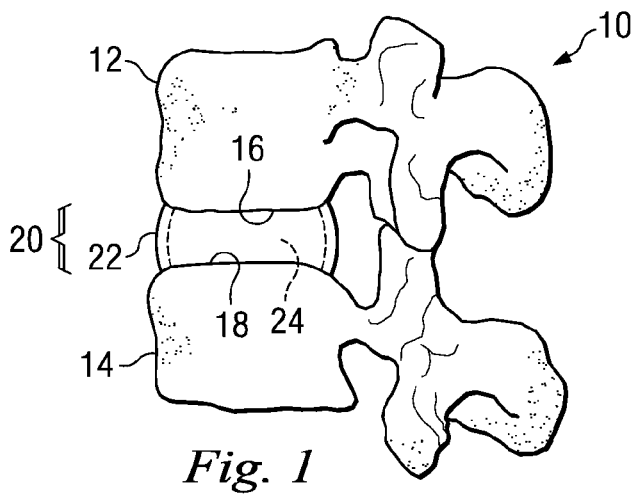
FIG. 1 is a sagittal view of a section of a vertebral column.
Figure 2:
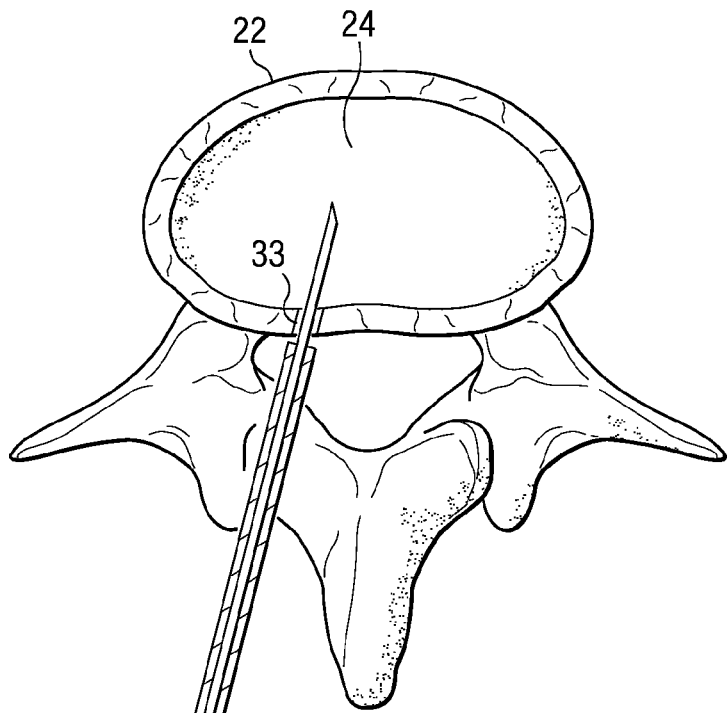
FIGS. 2-5 are a sequence of views of an intervertebral disc treatment including accessing the nucleus, inserting an expandable device, expanding the expandable device to create a space, and filling the space.

The present disclosure relates generally to devices, methods and apparatus for augmenting an intervertebral disc, and more particularly, to methods and instruments for minimally invasive access procedures. For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Referring first to FIG. 1, the reference numeral 10 refers to a vertebral joint section or a motion segment of a vertebral column. The joint section 10 includes adjacent vertebral bodies 12, 14. The vertebral bodies 12, 14 include endplates 16, 18, respectively. An intervertebral disc space 20 is located between the endplates 16, 18, and an annulus 22 surrounds the space 20. In a healthy joint, the space 20 contains a nucleus pulposus 24.

Referring now to FIGS. 2-5, in this embodiment, the nucleus 24 may be accessed by inserting a cannula 30 into the patient and locating the cannula at or near the annulus 22. An accessing instrument 32, such as a trocar needle or a K-wire is inserted through the cannula 30 and used to penetrate the annulus 22, creating an annular opening 33. This accessing procedure may be repeated at another position on the annulus 22 using a cannula 34 to create an annular opening 35. With the openings 33, 35 created, the accessing instrument 32 may be removed and the cannulae 30, 34 left in place to provide passageway for additional instruments.

In this embodiment, the nucleus is accessed using a posterior bilateral approach. In alternative embodiments, the annulus may be accessed with a lateral approach, an anterior approach, a trans-pedicular/vertebral endplate approach or any other suitable nucleus accessing approach. Although a bilateral approach is described, a unilateral or multi-lateral approach may be suitable. In another alternative embodiment, the nucleus 24 may be accessed through one the of vertebral bodies 12, 14 and through its respective endplate 16, 18. Thus, a suitable bilateral approach to nucleus augmentation may involve a combination approach including an annulus access opening and an endplate access opening.

It is understood that any cannulated instrument including a guide needle or a trocar sleeve may be used to guide the accessing instrument.

In this embodiment, the natural nucleus, or what remains of it after natural disease or degeneration, may remain intact with no tissue removed. In alternative embodiments, partial or complete nucleotomy procedures may be performed.

Figure 3:
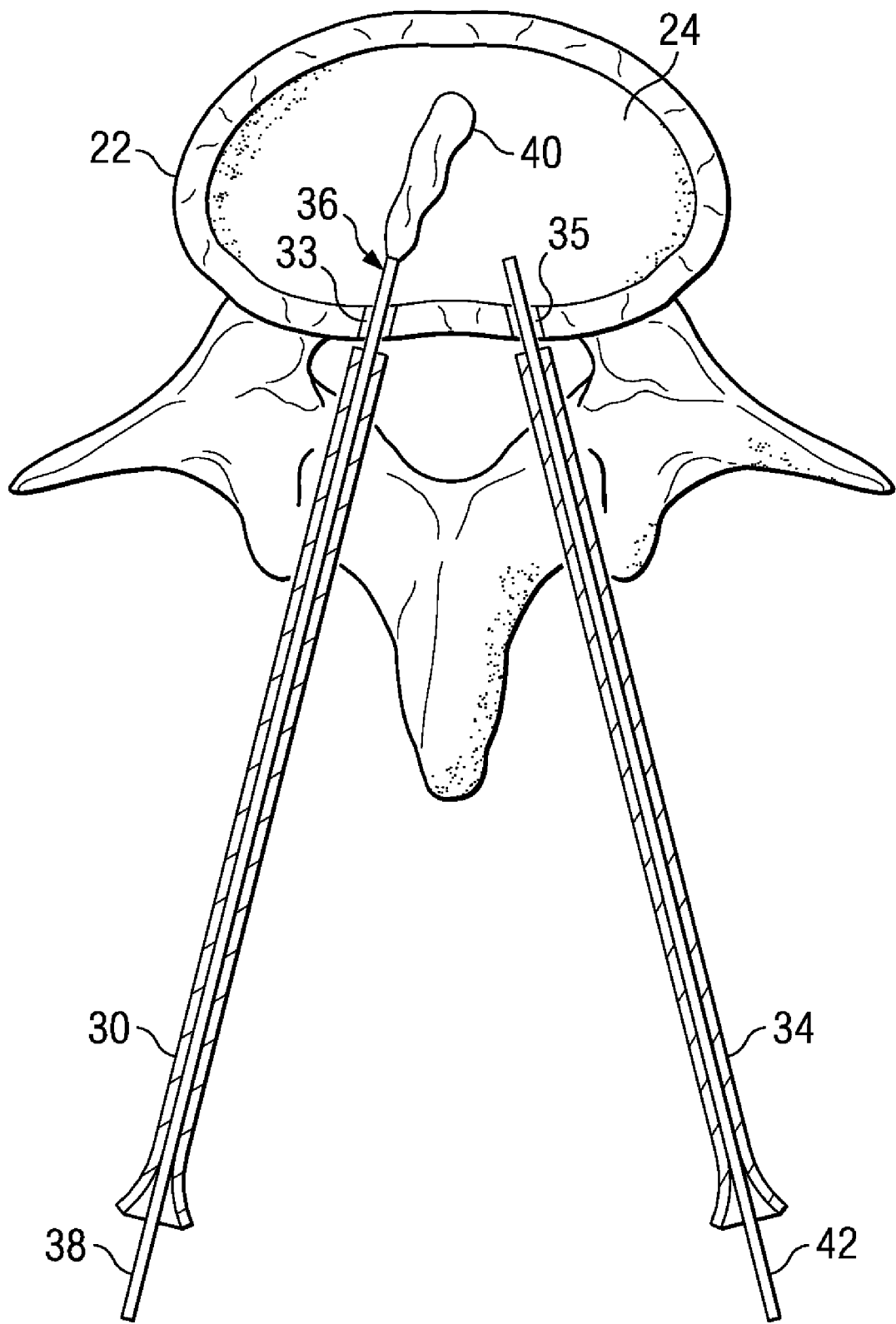

As shown in FIG. 3, a space creating device 36 having a catheter portion 38 and a spacing portion 40 may be inserted through the cannula 30 and the annular opening 33 into the nucleus 24. In this embodiment, the spacing portion 40 is an expandable device such as a balloon which may be formed of elastic or non-elastic materials. The balloon can be of various shapes including conical, spherical, square, long conical, long spherical, long square, tapered, stepped, dog bone, offset, or combinations thereof. Balloons can be made of various polymeric materials such as polyethylene terephthalates, polyolefins, polyurethanes, nylon, polyvinyl chloride, silicone, polyetheretherketone, polylactide, polyglycolide, poly (lactide-co-glycoli-de), poly(dioxanone), poly(.epsilon.-caprolactone), poly(hydroxylbutyrate), poly (hydroxylvalerate), tyrosine-based polycarbonate, polypropylene fumarate or combinations thereof. Additionally, the expandable device may be molded or woven.

In an alternative embodiment, the spacing portion may be mechanical instrument such as a probe or a tamp. A mechanically actuated deformable or expandable instrument which may deform via hinges, springs, shape memory material, etc. may also be used as a spacing portion. In some embodiments, the passage of the spacing portion may be aided with a more rigid guide needle or cannula which will accompany the spacing portion through the cannula and the annulus opening. This guide may be removed after the spacing portion is located within the nucleus 24.

As also shown in FIG. 3, a delivery instrument 42 may be passed through the cannula 34, through the annular opening 35, and into the nucleus 24. The delivery instrument 42 may be an injection needle or other material delivery instrument and may be blunt to avoid puncture or damage to the spacing portion 40.

Figure 4:
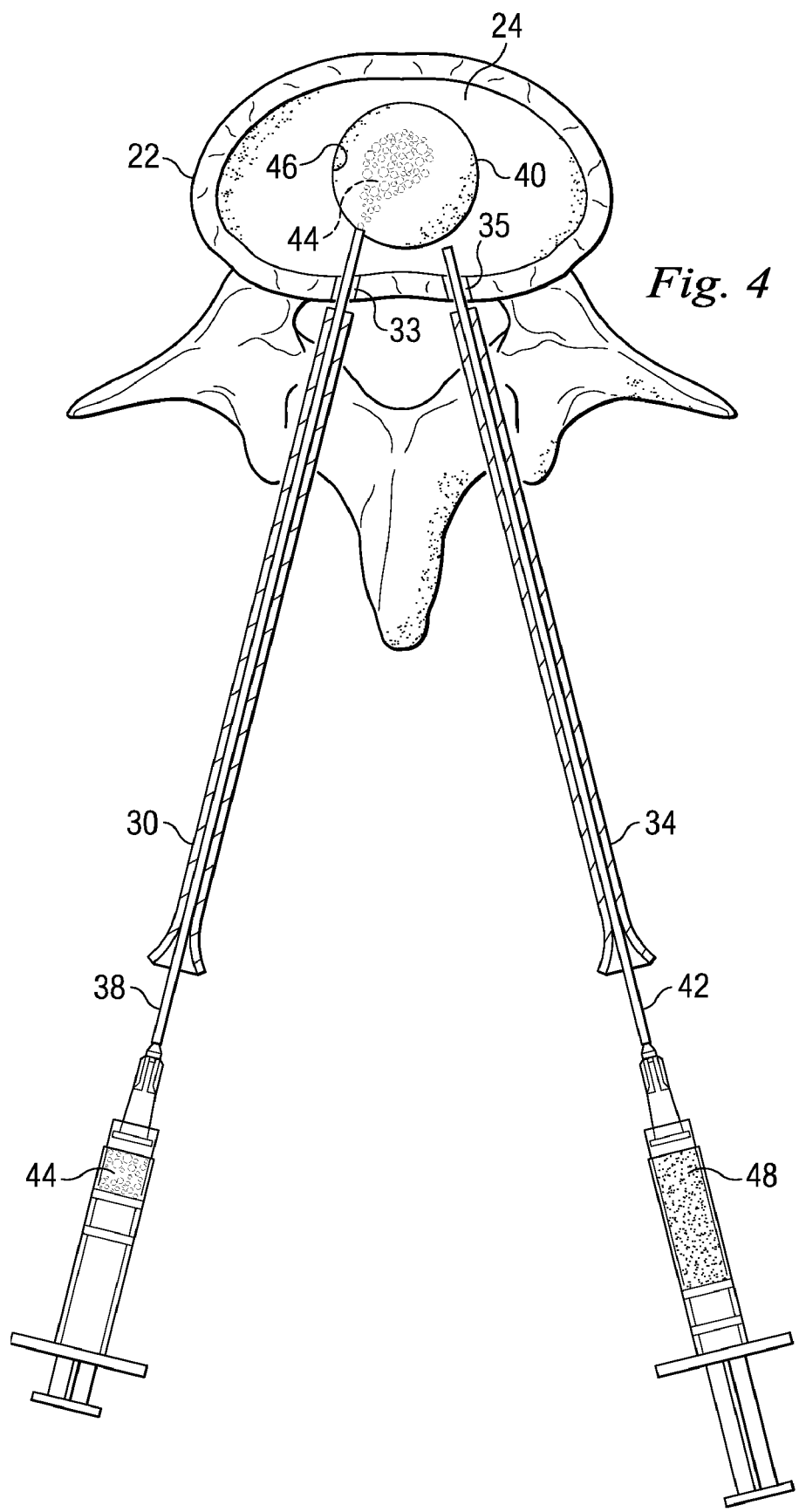
Figure 5:
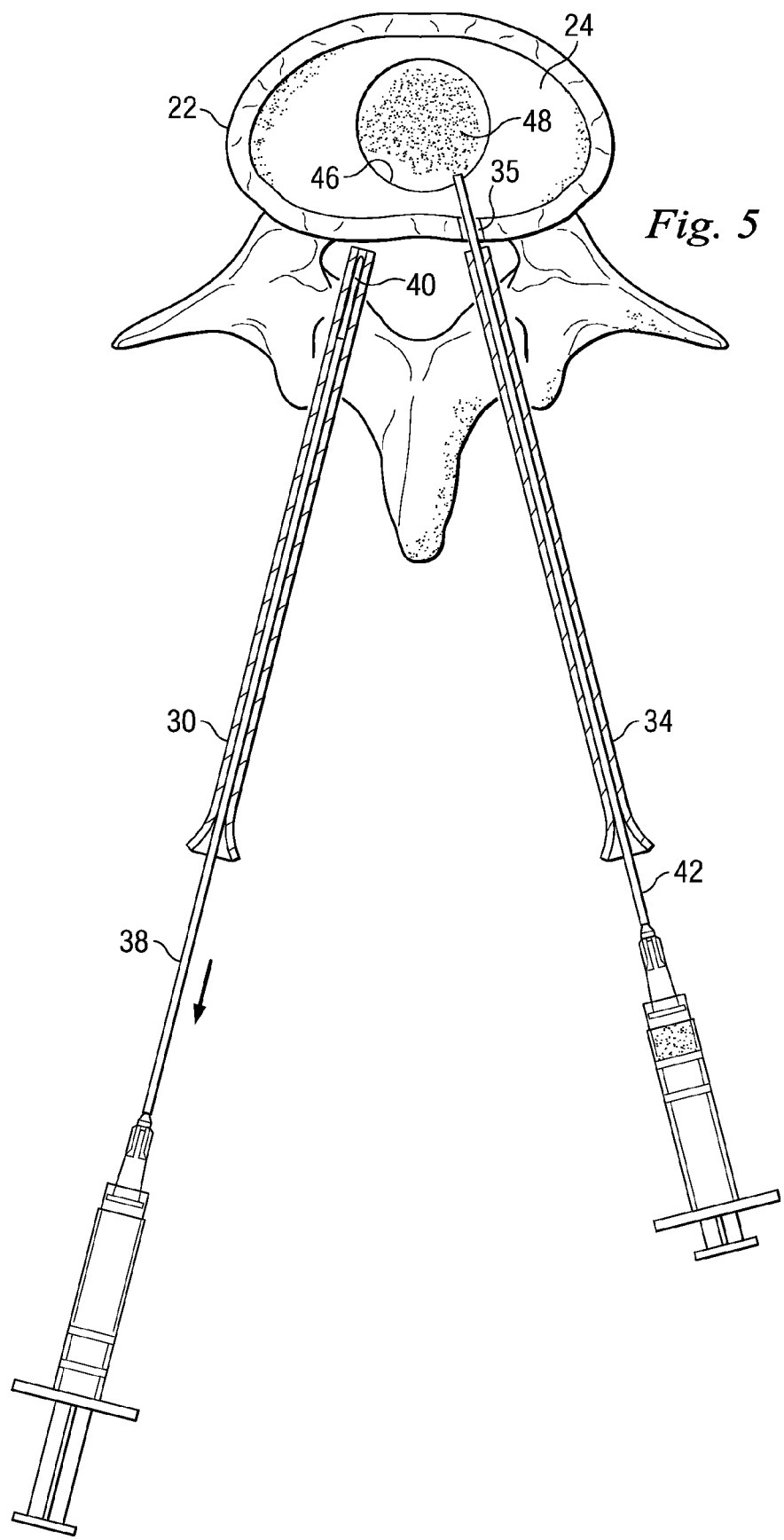

Referring now to FIG. 4, an inflation medium 44 may be pressurized and injected or otherwise passed through the catheter portion 38 of the space creating device 36 to pressurize and inflate the spacing portion 40. The inflation medium 44 may be a saline and/or radiographic contrast medium such as sodium diatrizoate solution sold under the trademark Hypaque® by Amersham Health, a division of GE Healthcare (Amersham, UK). The inflation medium 44 may be injected under pressure supplied by a hand, electric, or other type of powered pressurization device. The internal balloon pressure may be monitored with a well known pressure gauge. The rate of inflation and the pattern, size, or shape of the spacing portion 40 can be varied between patients depending on disc condition. A control device for controlling inflation and dispensing of material is described in further detail in U.S. patent application Ser. No. 11/412,558, entitled "DEVICES, APPARATUS, AND METHODS FOR IMPROVED DISC AUGMENTATION," filed Apr. 27, 2006, which is herein incorporated by reference in its entirety.

As the spacing portion 40 is gradually inflated, a space 46 is created in the nucleus tissue with the surrounding nucleus tissue becoming displaced or stretched. The inflation may also cause the intradiscal pressure to increase. Both the pressure increase and the direct expansion of the portion 40 may cause the endplates 16, 18 to distract. A pressure gauge and/or a pressure limiter may be used to avoid over inflation or excessive injection.

In an alternative embodiment, the space creating portion may be disposed within the annular opening 33 such that as the space creating portion is expanded, the opening becomes stretched or dilated by the space creating device.

After the space 46 is created, the space creating portion 40 is deflated leaving the space 46 to be filled by a biocompatible material 48 injected from the delivery instrument 42. The injection of the material 48 may be facilitated by using a pressurization device and monitoring gauge. The material 48 may be injected after the space creating portion 40 has been deflated and removed or may be injected while the space creating portion 40 is being deflated and removed. For example, the biomaterial 48 may become increasingly pressurized while the pressure in the space creating portion 40 is lowered. In some procedures, the material 48 may be injected before the space creating portion 40 is removed.

Examples of biocompatible materials 48 which may be used for disc augmentation include natural or synthetic and resorbable or non-resorbable materials. Natural materials include various forms of collagen that are derived from collagen-rich or connective tissues such as an intervertebral disc, fascia, ligament, tendon, skin, or demineralized bone matrix. Material sources include autograft, allograft, xenograft, or human-recombinant origin materials. Natural materials also include various forms of polysaccharides that are derived from animals or vegetation such as hyaluronic acid, chitosan, cellulose, or agar. Other natural materials include other proteins such as fibrin, albumin, silk, elastin and keratin. Synthetic materials include various implantable polymers or hydrogels such as silicone, polyurethane, silicone-polyurethane copolymers, polyolefin, polyester, polyacrylamide, polyacrylic acid, polyvinyl alcohol, polyethylene oxide, polyethylene glycol, polylactide, polyglycolide, poly(lactide-co-glycolide), poly(dioxanone), poly(.epsilon.-caprolactone), poly(hydroxylbutyrate), poly(hydroxylvalerate), tyrosine-based polycarbonate, polypropylene fumarate or combinations thereof. Suitable hydrogels may include poly (vinyl alcohol), poly(acrylic acids), poly(methacrylic acids), copolymers of acrylic acid and methacrylic acid, poly(acrylonitrile-acrylic acid), polyacrylamides, poly(N-vinyl-2-pyrrolidone), polyethylene glycol, polyethyleneoxide, polyacrylates, poly(2-hydroxy ethyl methacrylate), copolymers of acrylates with N-vinyl pyrrolidone, N-vinyl lactams, polyurethanes, polyphosphazenes, poly(oxyethylene)-poly(oxypropylene) block polymers, poly(oxyethylene)-poly(oxypropylene) block polymers of ethylene diamine, poly(vinyl acetate), and sulfonated polymers, polysaccharides, proteins, and combinations thereof.

The selected biocompatible material may be curable or polymerizable in situ. The biocompatible material may transition from a flowable to a non-flowable state shortly after injection. One way to achieve this transition is by adding a crosslinking agent to the biomaterial before, during, or after injection. The biocompatible material in its final state may be load-bearing, partially load-bearing, or simply tissue augmenting with minimal or no load-bearing properties.

Proteoglycans may also be included in the injectable biocompatible material 48 to attract and/or bind water to keep the nucleus 24 hydrated. Regenerating agents may also be incorporated into the biocompatible material. An exemplary regenerating agent includes a growth factor. The growth factor can be generally suited to promote the formation of tissues, especially of the type(s) naturally occurring as components of an intervertebral disc. For example, the growth factor can promote the growth or viability of tissue or cell types occurring in the nucleus pulposus, such as nucleus pulposus cells and chondrocytes, as well as space filling cells, such as fibroblasts and connective tissue cells, such as ligament and tendon cells. Alternatively or in addition, the growth factor can promote the growth or viability of tissue types occurring in the annulus fibrosis, as well as space filling cells, such as fibroblasts and connective tissue cells, such as ligament and tendon cells. An exemplary growth factor can include transforming growth factor-β (TGF-β) or a member of the TGF-β superfamily, fibroblast growth factor (FGF) or a member of the FGF family, platelet derived growth factor (PDGF) or a member of the PDGF family, a member of the hedgehog family of proteins, interleukin, insulin-like growth factor (IGF) or a member of the IGF family, colony stimulating factor (CSF) or a member of the CSF family, growth differentiation factor (GDF), cartilage derived growth factor (CDGF), cartilage derived morphogenic proteins (CDMP), bone morphogenetic protein (BMP), or any combination thereof. In particular, an exemplary growth factor includes transforming growth factor P protein, bone morphogenetic protein, fibroblast growth factor, platelet-derived growth factor, insulin-like growth factor, or any combination thereof.

Therapeutic or biological agents may also be incorporated into the biomaterial. An exemplary therapeutic or biological agent can include a soluble tumor necrosis factor α-receptor, a pegylated soluble tumor necrosis factor α-receptor, a monoclonal antibody, a polyclonal antibody, an antibody fragment, a COX-2 inhibitor, a metalloprotease inhibitor, a glutamate antagonist, a glial cell derived neurotrophic factor, a B2 receptor antagonist, a substance P receptor (NK1) antagonist, a downstream regulatory element antagonistic modulator (DREAM), iNOS, a inhibitor of tetrodotoxin (TTX)-resistant Na+-channel receptor subtypes PN3 and SNS2, an inhibitor of interleukin, a TNF binding protein, a dominant-negative TNF variant, Nanobodies™, a kinase inhibitor, or any combination thereof.

These regenerating, therapeutic, or biological agents may promote healing, repair, regeneration and/or restoration of the disc, and/or facilitate proper disc function. Additives appropriate for use in the claimed invention are known to persons skilled in the art, and may be selected without undue experimentation.

After the biocompatible material 48 is injected, the delivery instrument 42 may be removed from the cannula 34. If the selected biocompatible material 48 is curable in situ, the instrument 42 may be removed during or after curing to minimize leakage. The openings 33, 35 may be small enough, for example less than 3 mm, that they will close or close sufficiently that the injected biocompatible material 48 will remain within the annulus. The use of an annulus closure device such as a suture, a plug, or a material sealant is optional. The cannulae 30, 34 may be removed and the minimally invasive surgical incision closed.

Any of the steps of the method including expansion of the space creating portion 40 and filling the space 46 may be monitored and guided with the aid of imaging methods such as fluoroscopy, x-ray, computed tomography, magnetic resonance imaging, and/or image guided surgical technology such as a Stealth Station™ surgical navigation system (Medtronic, Inc., Minneapolis, Minn.) or a BrainLab system (Heimstetten, Germany).

In an alternative embodiment, the space creating portion may be detachable from the catheter portion and may remain in the nucleus 24 as an implant. In this alternative, the biocompatible material may be injected directly into the space creating portion.

Figure 6:
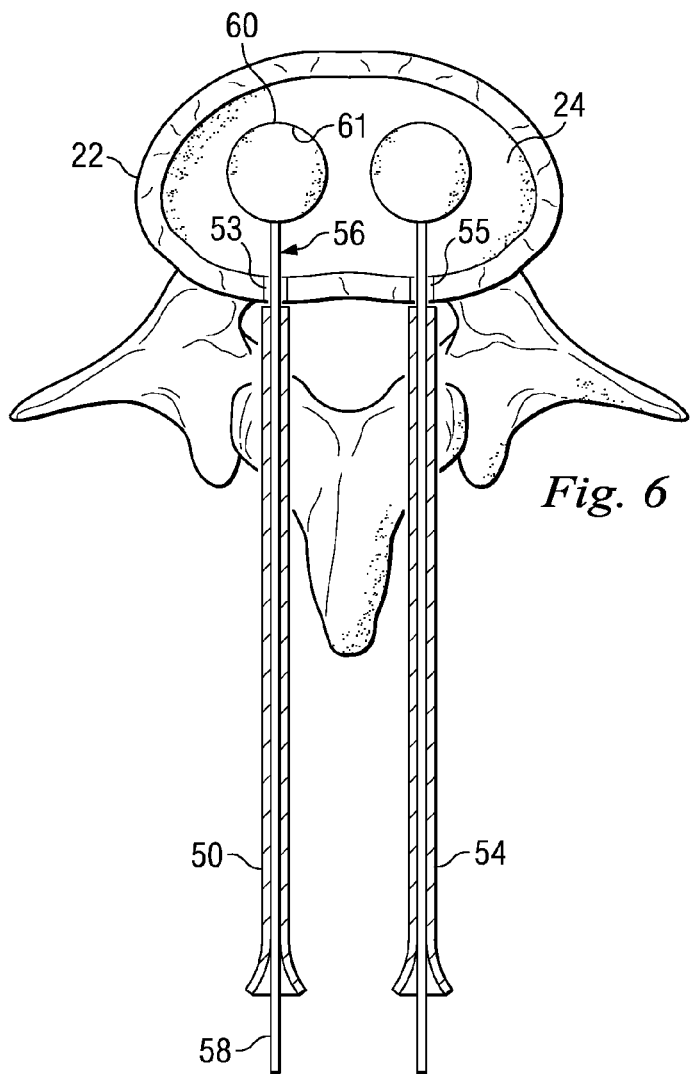
FIGS. 6-7 are sequence views of an intervertebral disc treatment according to another embodiment of the present disclosure.
Figure 7:
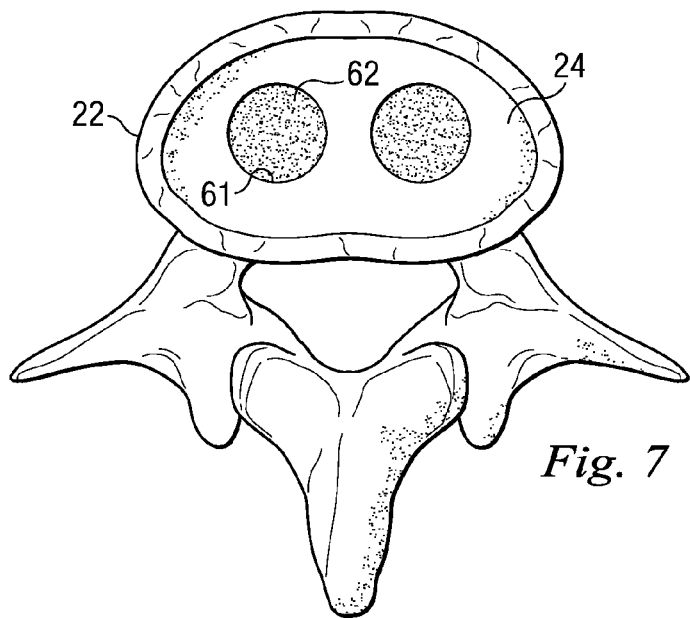

Referring now to FIGS. 6-7, in this embodiment, the nucleus 24 may be accessed by inserting a cannula 50 into the patient and locating the cannula at or near the annulus 22. As described above, an accessing instrument is inserted through the cannula 50 and used to penetrate the annulus 22, creating an annular opening 53. This accessing procedure may be repeated at another position on the annulus 22 using a cannula 54 to create an annular opening 55. With the openings 53, 55 created, the accessing instrument may be removed and the cannulae 50, 54 left in place to provide bilateral passageways for additional instruments. In this embodiment, the natural nucleus, or what remains of it after natural disease or degeneration, may remain intact with no tissue removed. In alternative embodiments, partial or complete nucleotomy procedures may be performed.

As shown in FIG. 6, a space creating device 56 having a catheter portion 58 and a spacing portion 60 may be inserted through the cannula 50 and the annular opening 53 into the nucleus 24. In this embodiment, the spacing portion is an expandable device such as a balloon which may be formed of elastic or non-elastic materials. The characteristics of the balloon may be the same or similar to those described above. The spacing portion may be inflated and removed as described in further detail in U.S. patent application Ser. No. 10/314,396 ("the '396 application") which is incorporated herein by reference. The space 61 created by the spacing portion may be filled with a biocompatible material 62 using the cannula 54 through the bilateral opening 55 in a manner similar to that described above for FIGS. 2-5 or alternatively, using the same cannula 50 and the opening 53 in a manner similar to that described in the '396 application. The procedure of creating a space in the nucleus 24 may be repeated in another location of the nucleus using the annular opening 55 to pass a space creating device for creating a second space to be filled with a biocompatible material. This procedure may be substantially similar to that described above for creating and filling space 61.

Figure 8:
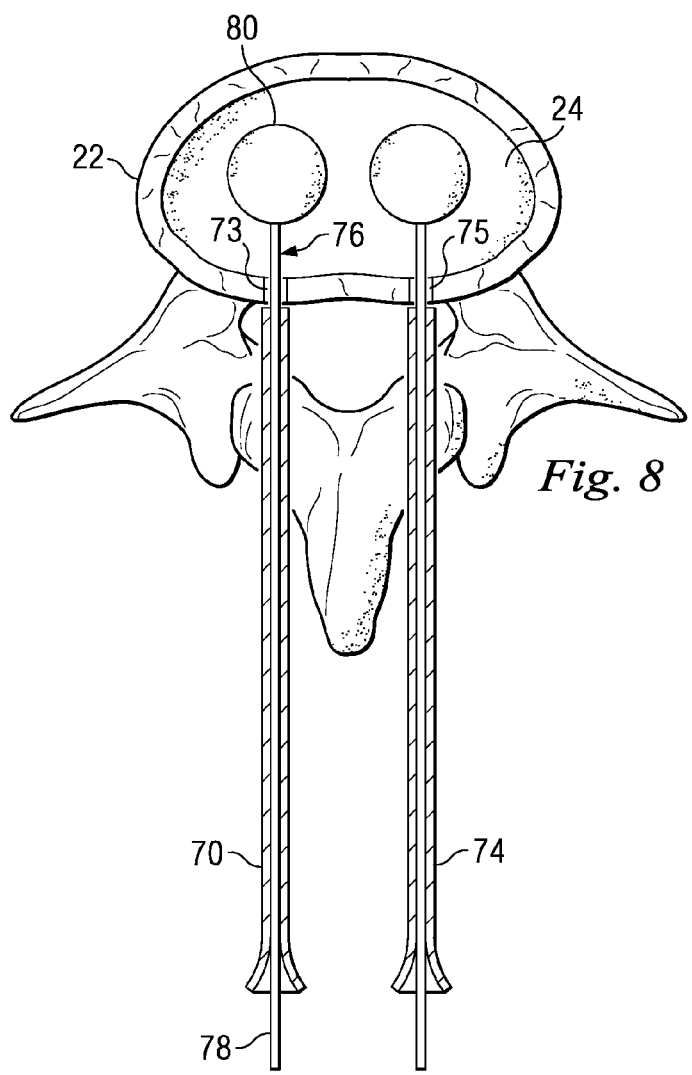
FIGS. 8-9 are sequence views of an intervertebral disc treatment according to another embodiment of the present disclosure.
Figure 9:
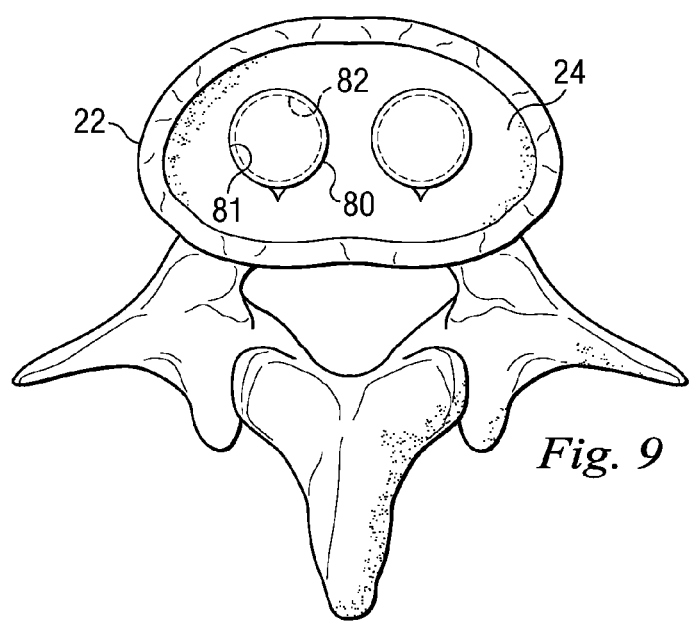

Referring now to FIGS. 8-9, in this embodiment, the nucleus 24 may be accessed by inserting a cannula 70 into the patient and locating the cannula at or near the annulus 22. As described above, an accessing instrument is inserted through the cannula 70 and used to penetrate the annulus 22, creating an annular opening 73. This accessing procedure may be repeated at another position on the annulus 22 using a cannula 74 to create an annular opening 75. With the openings 73, 75 created, the accessing instrument may be removed and the cannulae 70, 74 left in place to provide bilateral passageways for additional instruments. In this embodiment, the natural nucleus, or what remains of it after natural disease or degeneration, may remain intact with no tissue removed. In alternative embodiments, partial or complete nucleotomy procedures may be performed.

As shown in FIG. 8, a space creating device 76 having a catheter portion 78 and a spacing portion 80 may be inserted through the cannula 70 and the annular opening 73 into the nucleus 24. In this embodiment, the spacing portion is an expandable device such as a balloon which may be formed of elastic or non-elastic materials. The characteristics of the balloon may be the same or similar to those described above. The spacing portion 80 may be pressurized and filled with a biocompatible material 82 as described in further detail in the '396 application. In this embodiment, the filled spacing portion 80 may be detached and left within the nucleus pulposus 24 as an implant. The procedure of creating a space in the nucleus 24 may be repeated in another location of the nucleus using the annular opening 55 to pass a spacing portion for creating a second space, filling the spacing portion with a biocompatible material, and detaching the second spacing portion. This procedure may be substantially similar to the procedure for filling the spacing portion 80. In an alternative embodiment, the spacing portion may be filled with a biocompatible material using the cannula 74 and the bilateral opening 75 in a manner similar to that described above for FIGS. 2-5. This delivery of material through the bilateral opening 75 may occur either before or after the spacing portion is detached from the catheter portion of the space creating device.

Figure 10:
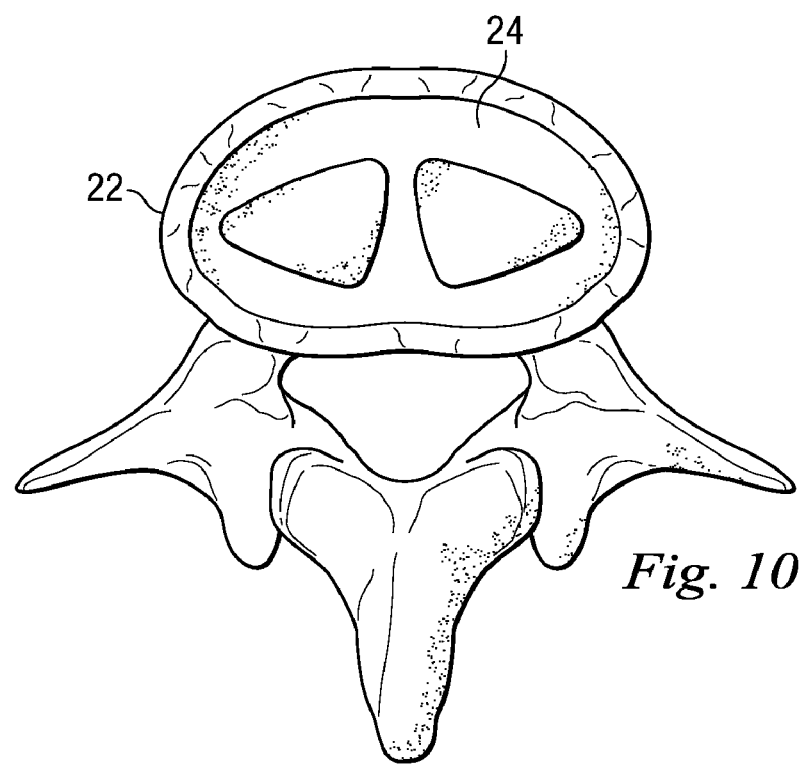
FIGS. 10-11 are alternative intervertebral disc treatments according to other embodiments of the present disclosure.
Figure 11:
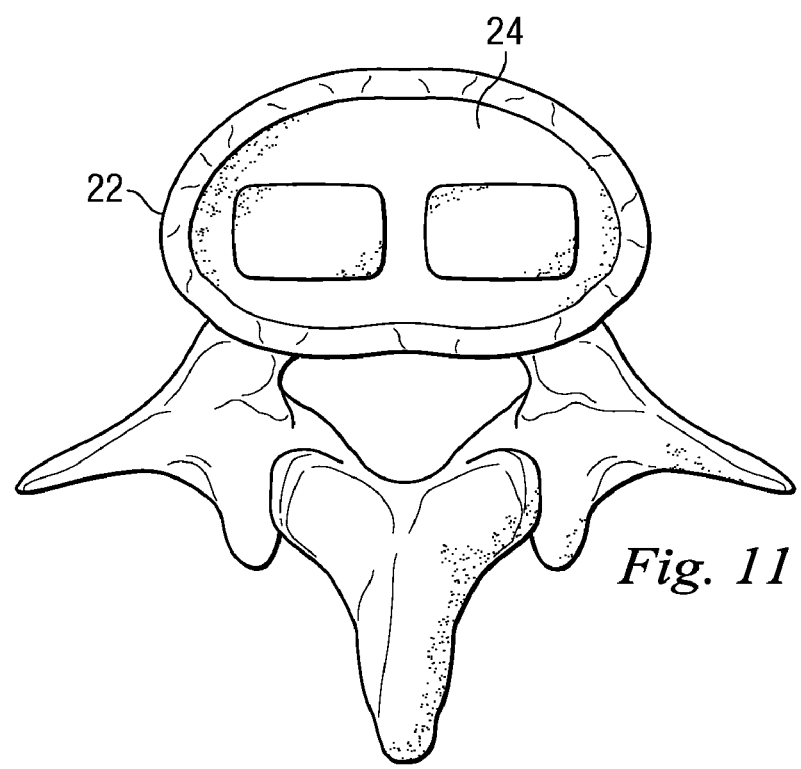

Referring now to FIGS. 10 and 11, spacing portions similar to those described in the previous embodiments may be preformed in various shapes, such as triangular (FIG. 10) or capsular (FIG. 11), to achieve patient-specific goals including compensating for unique nucleus degradation or patient-tailored endplate distraction.

Figure 12:
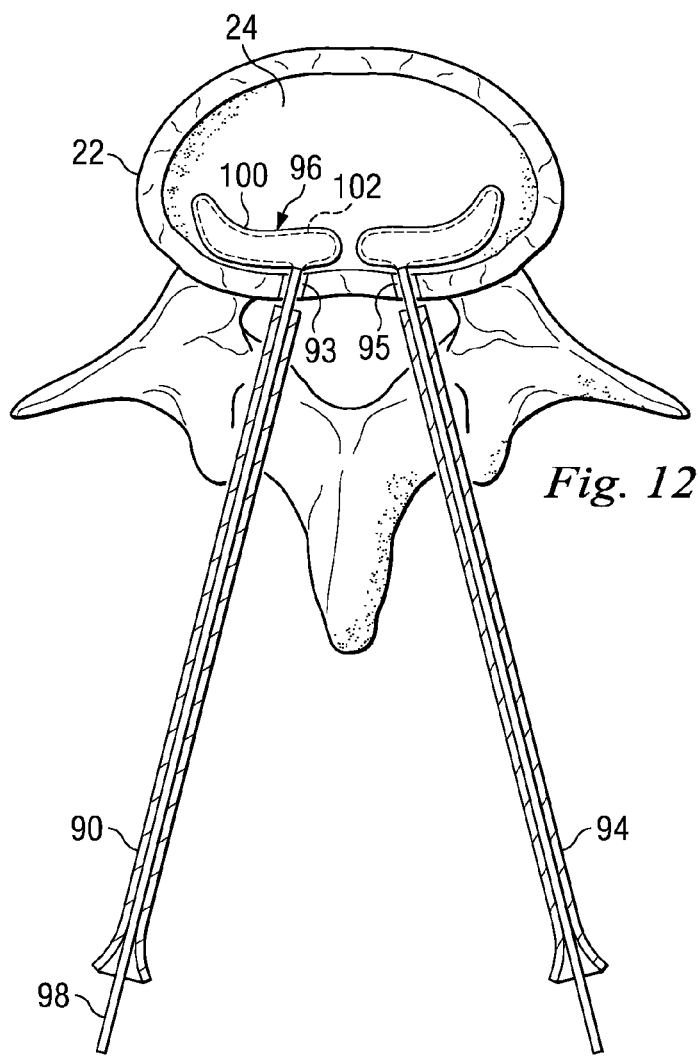
FIGS. 12-13 are sequence views of an intervertebral disc treatment according to another embodiment of the present disclosure.
Figure 13:
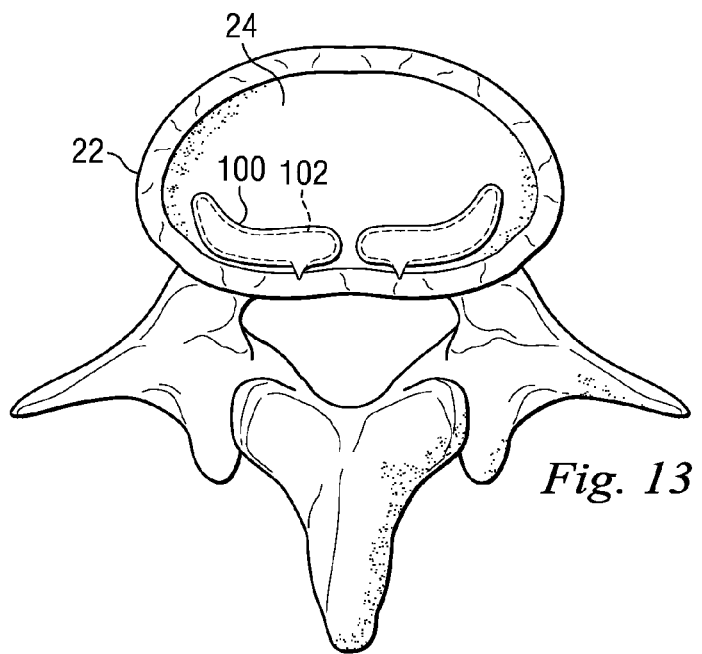

Referring now to FIGS. 12 and 13, in this embodiment, the nucleus 24 may be accessed by inserting a cannula 90 into the patient and locating the cannula at or near the annulus 22. As described above, an accessing instrument is inserted through the cannula 90 and used to penetrate the annulus 22, creating an annular opening 93. This accessing procedure may be repeated at another position on the annulus 22 using a cannula 94 to create an annular opening 95. With the openings 93, 95 created, the accessing instrument may be removed and the cannulae 90, 94 left in place to provide bilateral passageways for additional instruments. In this embodiment, the natural nucleus, or what remains of it after natural disease or degeneration, may remain intact with no tissue removed. In alternative embodiments, partial or complete nucleotomy procedures may be performed.

As shown in FIG. 12, a space creating device 96 having a catheter portion 98 and a spacing portion 100 may be inserted through the cannula 90 and the annular opening 93 into the nucleus 24. In this embodiment, the spacing portion 100 is an expandable device such as a balloon which may be formed of elastic or non-elastic materials. The characteristics of the balloon may be the same or similar to those described above. The balloon may be shaped to fit along the inner contour of the annulus 22. The spacing portion 100 may be pressurized, filled, and detached as described above. The spacing portion 100 may be filled with a biocompatible material 102 using the cannula 94 and the bilateral opening 95 in a manner similar to that described above for FIGS. 2-5 or using the same cannula 90 and the opening 93 in a manner similar to that described in the '396 application. The procedure of creating a space in the nucleus 24 along the annulus 22 may be repeated in another location of the nucleus using the annular opening 55 to pass a space creating device for creating a second implant to be filled with a biocompatible material. This procedure may be substantially similar to that described above for creating and filling spacing portion 100. The implant created by the filled spacing portion 100 and its bilateral counterpart may be contoured to fit along an interior segment of annulus 22. The resulting implant may support a weakened annulus or reinforce a ruptured annulus to reduce or prevent nucleus herniation. The biocompatible material may be selected to optimize support and flexibility.

Figure 14:
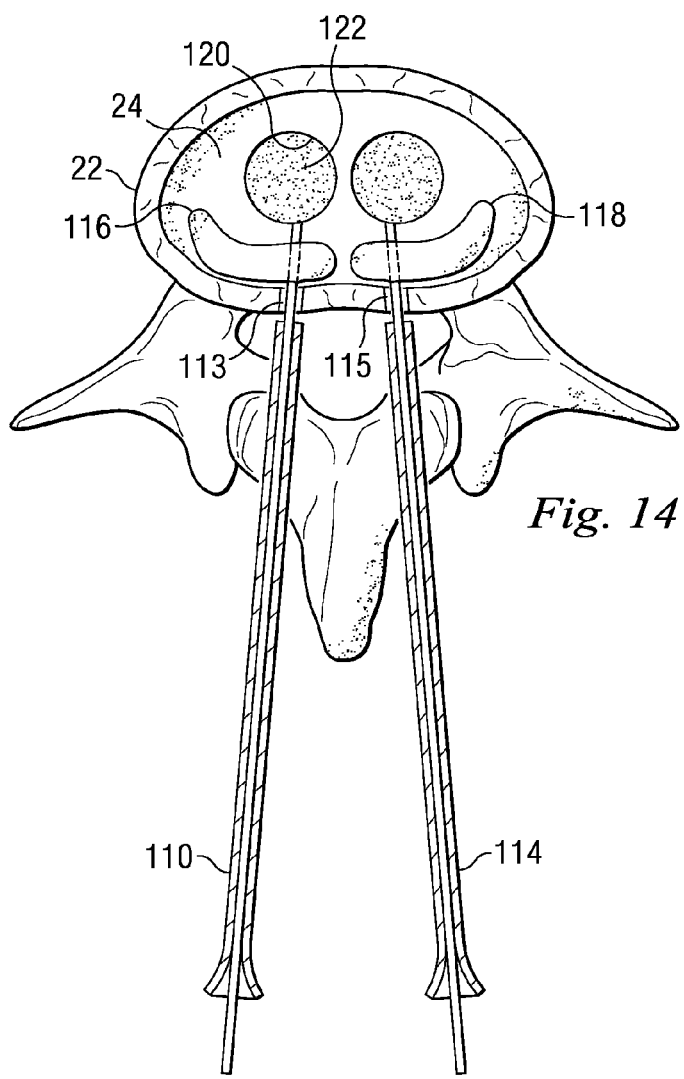
FIGS. 14-15 are sequence views of an intervertebral disc treatment according to another embodiment of the present disclosure.
Figure 15:
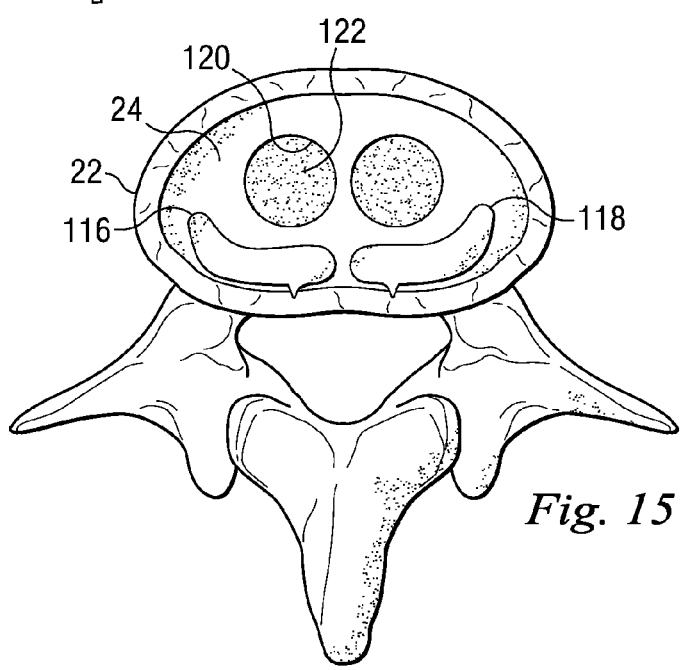

Referring now to FIGS. 14 and 15, in this embodiment, the nucleus 24 may be accessed by inserting a cannula 110 into the patient and locating the cannula at or near the annulus 22. As described above, an accessing instrument is inserted through the cannula 110 and used to penetrate the annulus 22, creating an annular opening 113. This accessing procedure may be repeated at another position on the annulus 22 using a cannula 114 to create an annular opening 115. With the openings 113, 115 created, the accessing instrument may be removed and the cannulae 110, 114 left in place to provide bilateral passageways for additional instruments. In this embodiment, the natural nucleus, or what remains of it after natural disease or degeneration, may remain intact with no tissue removed. In alternative embodiments, partial or complete nucleotomy procedures may be performed.

As shown in FIG. 14, annulus contoured spacing portions 116, 118 may be inserted, detached, and filled as described above in FIG. 12. The resulting implant may support a weakened annulus or reinforce a ruptured annulus to reduce or prevent nucleus herniation. The biocompatible filling material may be selected to optimize support and flexibility. These annulus reinforcing spacing portions 116, 118 may be used in conjunction with the more centralized nucleus spacing procedures described in FIGS. 2-11. In this embodiment, an additional spacing portion may be inserted through the filled spacing portions 116, 118 and expanded within the nucleus 24 to create a space 120. The space 120 may be filled with a biomaterial 122. More spacing portions may be inserted to create additional filled spaces in the nucleus 24. The use of annular spacing portions in conjunction with more centralized spacing portions may help to prevent the more centralized biomaterial and the natural nucleus tissue from migrating through annular defects or openings. The biomaterials selected for filling the various spaces and spacing portions may be the same or different depending upon the desired result.

In an alternative embodiment, a delivery instrument may be inserted through the spacing portions 116, 118 to deposit a biocompatible material directly into the nucleus 24 without creating an additional space within the nucleus. In this embodiment, the spacing portions serve to block migration or expulsion of the biocompatible material through the annulus, however the material may be more dispersed within the nucleus rather than concentrated in a pre-formed space.

Figure 16:
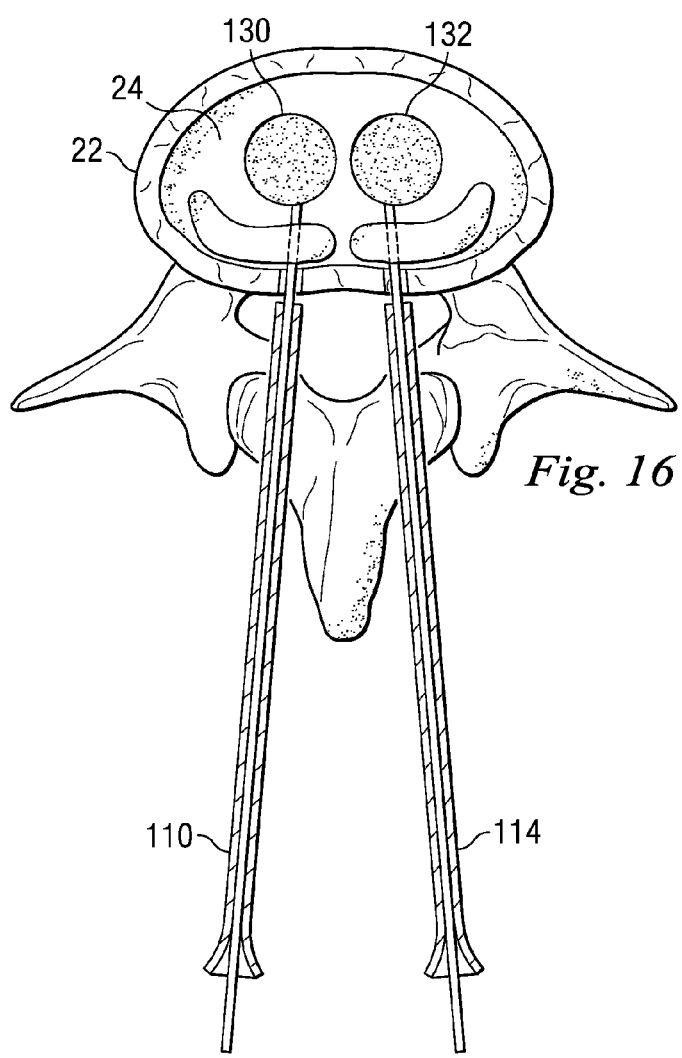
FIGS. 16-17 are sequence views of an intervertebral disc treatment according to another embodiment of the present disclosure.
Figure 17:
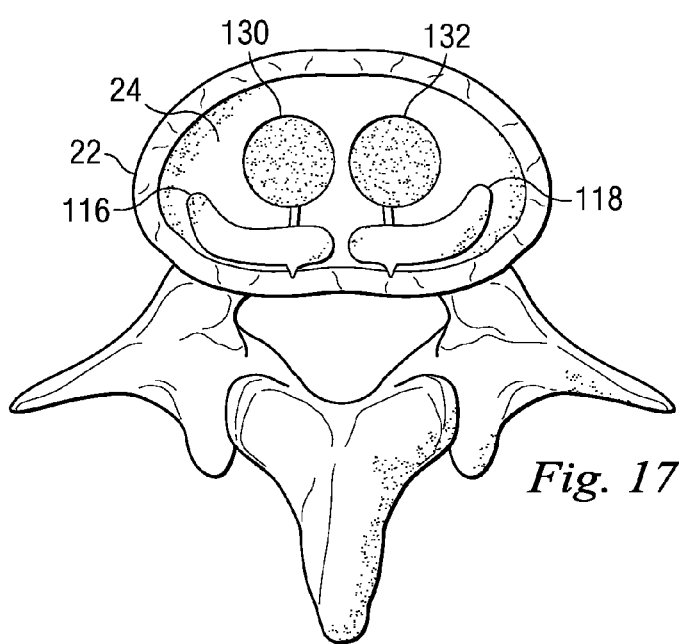

Referring now to FIGS. 16-17, in this embodiment, a substantially similar method of nucleus augmentation as the procedure described above for FIGS. 14-15 may be performed. In this embodiment, however, as described in FIGS. 8-9, spacing portions 130, 132 for creating the more centralized nucleus spaces may be detached to remain in the nucleus tissue as implants.

Figure 18:
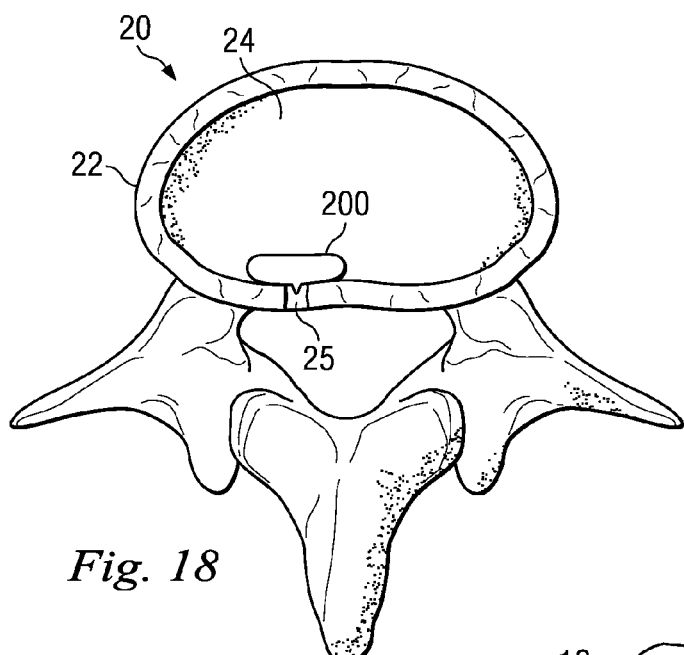
FIG. 18 is top view of an expandable intervertebral treatment device disposed within an intervertebral disc according to another embodiment of the present disclosure.
Figure 19:
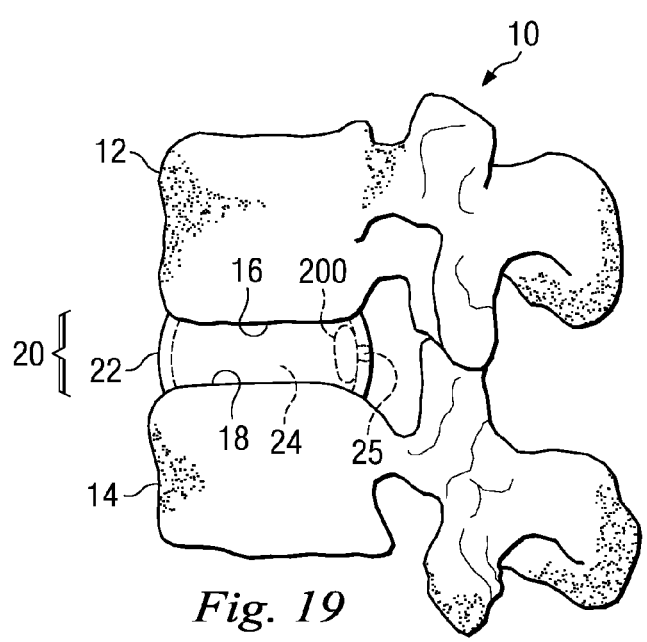
FIG. 19 is a lateral view of the expandable intervertebral treatment device of FIG. 18.
Figure 20:
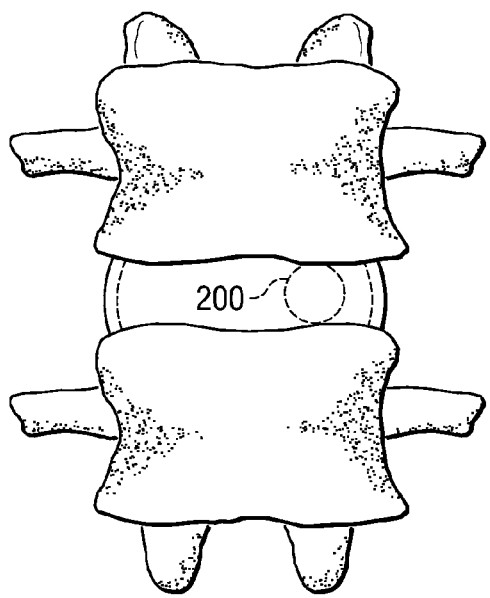
FIG. 20 is an anterior view of the expandable intervertebral treatment device of FIG. 18.

Referring now to FIGS. 18-20, shown therein is an expandable intervertebral treatment device 200 disposed within an intervertebral disc 20 according to another embodiment of the present disclosure. The device 200 is adapted to treat a defect 25 in the annulus 22. FIG. 18 is a top-down view; FIG. 19 is a lateral view; and FIG. 20 is an anterior view. In this embodiment, the device 200 is an expandable device, such as a balloon, that has a predetermined expanded shape. In the present embodiment, the predetermined expanded shape is a circular disc. The device 200 has substantially circular profile when viewed anteriorly as in FIG. 20. In other embodiments and as described below, the device 200 has other anterior profiles including other geometrical, arcuate, and/or irregular shapes in other embodiments. Further, the device has substantially oblong inferior and lateral profiles, as shown in FIGS. 18 and 19 respectively. In other embodiments, the device 200 has other inferior and/or lateral profiles including other geometrical, arcuate, and/or irregular shapes.

In some aspects, the characteristics of the device 200 may be the same or similar to those described above. The device 200 may be formed of elastic or non-elastic materials. The device 200 may be configured as a balloon, pouch, or envelope. The device 200 may be a uniform material or may be braided, woven, knitted or otherwise constructed to contain biocompatible material. The device 200 may be shaped or contoured to fit along the inner contour of the annulus 22. In particular, the device 200 may be shaped or contoured to substantially cover or seal the defect 25 in the annulus 22. The device 200 may be pressurized, filled, and detached as described above. The final dimensions (such as the diameter) of the filled device 200 may be at least twice the size of the defect 25, although dimensions that are at least three times the original dimensions may also be suitable. The device 200 may have a greater expansion in a direction along the inner annulus than toward the center of the nucleus pulposus. The device 200 may be filled with a biocompatible material using the cannula and the bilateral opening in a manner similar to that described above for FIGS. 2-5, or using the same cannula and the opening in a manner similar to that described in the '396 application. The procedure of creating a space in the nucleus 24 along the annulus 22 may be repeated in another location of the nucleus to pass a second device for creating a second implant to be filled with a biocompatible material. For example, a second device may be used in combination with the device 200 in a bilateral procedure. In some aspects the device 200, and its bilateral counterpart in some embodiments, is curved along its length to substantially match the contour of an interior segment of annulus 22. The expanded device may support a weakened annulus, reinforce a ruptured annulus to reduce and/or prevent nucleus herniation, and/or treat a defect in the annulus. The biocompatible material may be selected to optimize the desired characteristics of the device 200.

Figure 21:
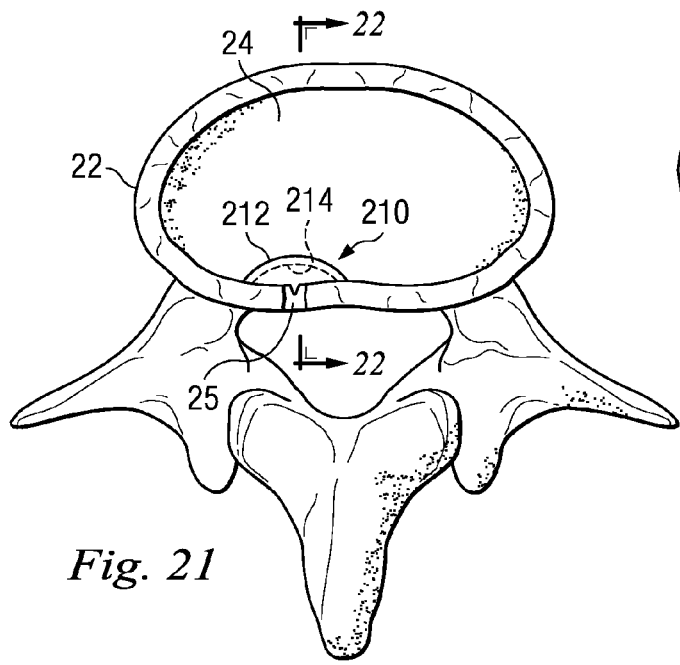
FIG. 21 is top view of an expandable intervertebral treatment device disposed within an intervertebral disc according to another embodiment of the present disclosure.
Figure 22:
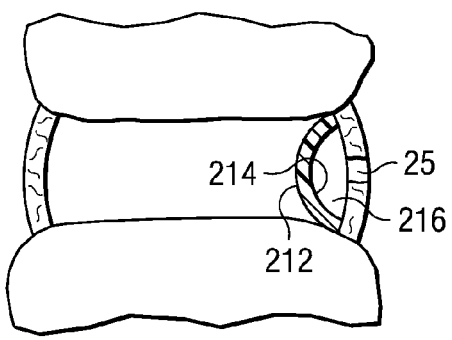
FIG. 22 is a cross-sectional side view of the intervertebral treatment device of FIG. 21 taken along section line 22-22.
Figure 24:
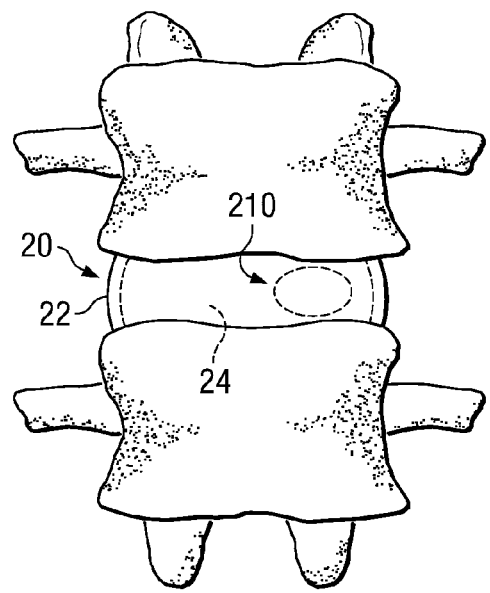
FIG. 24 is an anterior view of the expandable intervertebral treatment device of FIG. 21.
Figure 23:
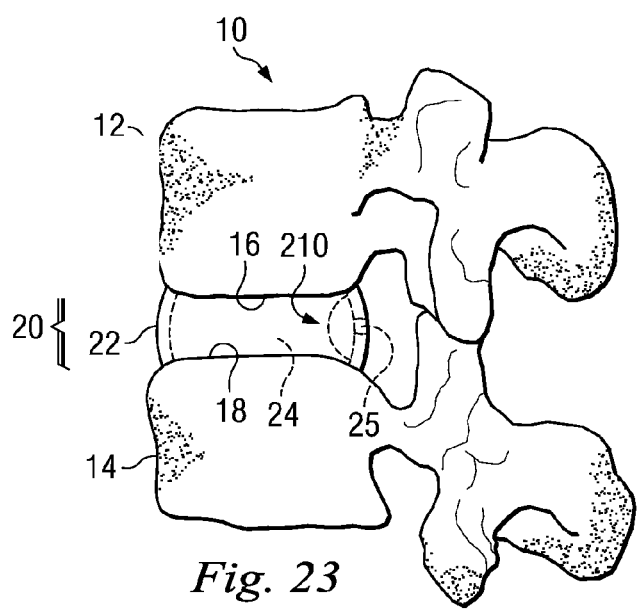
FIG. 23 is a lateral view of the expandable intervertebral treatment device of FIG. 21.

Referring now to FIGS. 21-24, shown therein is an expandable intervertebral treatment device 210 disposed within an intervertebral disc 20 according to another embodiment of the present disclosure. The device 210 is adapted to treat a defect 25 in the annulus 22. FIG. 21 is a top-down view; FIG. 22 is a cross-sectional lateral view taken along section line 22-22; FIG. 23 is a lateral view; and FIG. 24 is an anterior view. In this embodiment, the device 210 is an expandable device, such as a balloon, that has a predetermined expanded shape. In the present embodiment, the predetermined expanded shape is similar to a bowl or an expanded umbrella. That is, the device 210 when expanded has a substantially arcuate outer surface 212 and a substantially arcuate inner surface 214 such that a space 216 is present between the inner surface 214 and the inner wall of the annulus 22 when the device 210 is positioned against the annulus 22, as shown in FIG. 22. As shown, in the current embodiment the device 210 is positioned against the inner wall of the annulus 22 so as to separate the defect 25 from the remaining portion of the annulus and the nucleus pulposus 24.

The device 210 has substantially oblong profile when viewed anteriorly as in FIG. 24. In other embodiments and as described below, the device 210 has other anterior profiles including other geometrical, arcuate, and/or irregular shapes in other embodiments. Further, the device has substantially oblong inferior and lateral profiles, as shown in FIGS. 21 and 23 respectively. In other embodiments, the device 210 has other inferior and/or lateral profiles including other geometrical, arcuate, and/or irregular shapes. Similarly, the opening 216 has a substantially smooth arcuate contour defined by the inner surface 214 of the device 210, as shown in FIGS. 21 and 22. However, in other embodiments, the inner surface 214 may include various projections, recesses, and/or have a non-arcuate shape such that the opening 216 is defined likewise. Further, in some embodiments the inner surface 214 may have other geometrical, arcuate, and/or irregular shapes.

In some aspects, the characteristics of the device 210 may be the same or similar to those described above. The device 210 may be formed of elastic or non-elastic materials. The device 210 may be shaped or contoured to fit along the inner contour of the annulus 22. In particular, the device 210 may be shaped or contoured to substantially cover or seal the defect 25 in the annulus 22. The device 210 may be pressurized, filled, and detached as described above. The device 210 may be filled with a biocompatible material using the cannula and the bilateral opening in a manner similar to that described above for FIGS. 2-5, or using the same cannula and the opening in a manner similar to that described in the '396 application. The procedure of creating a space in the nucleus 24 along the annulus 22 may be repeated in another location of the nucleus to pass a second device for creating a second implant to be filled with a biocompatible material. For example, a second device may be used in combination with the device 210 in a bilateral procedure. In some aspects the device 210, and its bilateral counterpart in some embodiments, is curved along its length to substantially match the contour of an interior segment of annulus 22. The expanded device 210 may support a weakened annulus, reinforce a ruptured annulus to reduce and/or prevent nucleus herniation, and/or treat a defect in the annulus. The biocompatible material may be selected to optimize the desired characteristics of the device 210.

Figure 25:
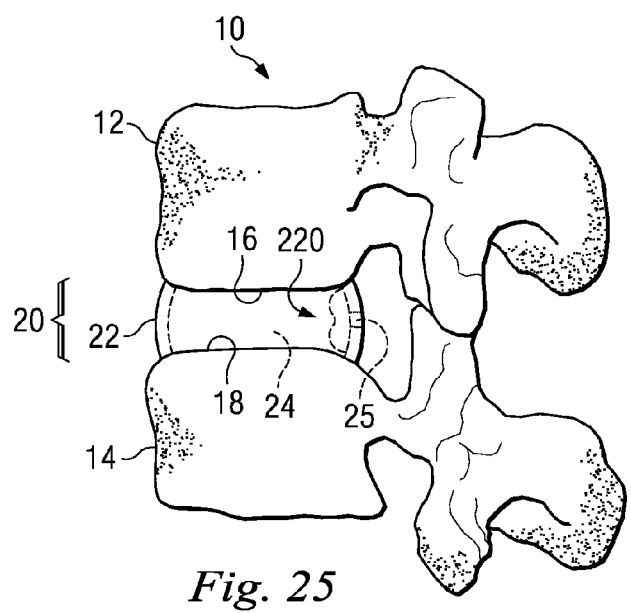
FIG. 25 is a lateral view of an expandable intervertebral treatment device disposed within an intervertebral disc according to another embodiment of the present disclosure.
Figure 26:
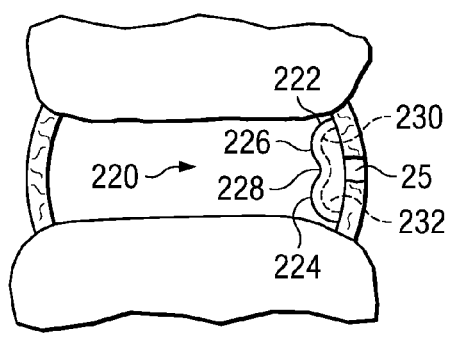
FIG. 26 is a cross-sectional side view of the intervertebral treatment device of FIG. 25.

Referring now to FIGS. 25-28, shown therein are alternative embodiments of an expandable intervertebral treatment device according to the present disclosure. In particular, the alternative embodiments shown in FIGS. 25-28 illustrate exemplary lateral profiles and/or lateral cross-sectional profiles according to some aspects of the present disclosure. Referring more specifically to FIGS. 25 and 26, an expandable intervertebral treatment device 220 is shown disposed within an intervertebral disc 20 according to another embodiment of the present disclosure. FIG. 25 is a lateral view; FIG. 26 is a cross-sectional lateral view. The device 220 is adapted to treat a defect 25 in the annulus 22. The device 220 may be substantially similar in some aspects to the devices described above.

In the current embodiment, the device 220 is an expandable device, such as a balloon, that has a predetermined expanded shape. In the present embodiment, the predetermined expanded shape includes an outer surface 222 having a pair of convex projections 224, 226 and a recess 228 disposed therebetween. In the current embodiment, the projections 224, 226 and the recess 228 are comprised of substantially arcuate curves. In other embodiments, the projections 224, 226 and/or the recess 228 have other geometrical, arcuate, planar, and/or irregular shapes. Further, in other embodiments the device 220 includes more or less projections and/or more or less recesses.

The device 220 also includes an inner surface 230 such that a space 232 is present between the inner surface 230 of the device and the inner wall of the annulus 22 when the device 220 is positioned against the annulus 22, as shown in FIG. 26. As shown, in the current embodiment the device 220 is positioned against the inner wall of the annulus 22 so as to separate the defect 25 from the remaining portion of the annulus and the nucleus pulposus 24. Further, the inner surface 230 substantially matches the contours of the outer surface 222 such that the inner surface 230 includes a pair of recesses corresponding the pair of projections 224, 226 and a projection corresponding to the recess 228. In this manner, the device 220 has a substantially constant thickness when filled with the biocompatible material. In other embodiments, the inner surface does not match the contours of the outer surface. Rather, the inner surface has other geometrical, arcuate, planar, and/or irregular shapes in other embodiments. Therefore, in other embodiments the opening 232 has other shapes corresponding to the contours of the inner surface. In some embodiments, the inner surface 230 is contoured to match the inner wall of the annulus 22 such that there is no space between the device and the annulus.

Figure 27:
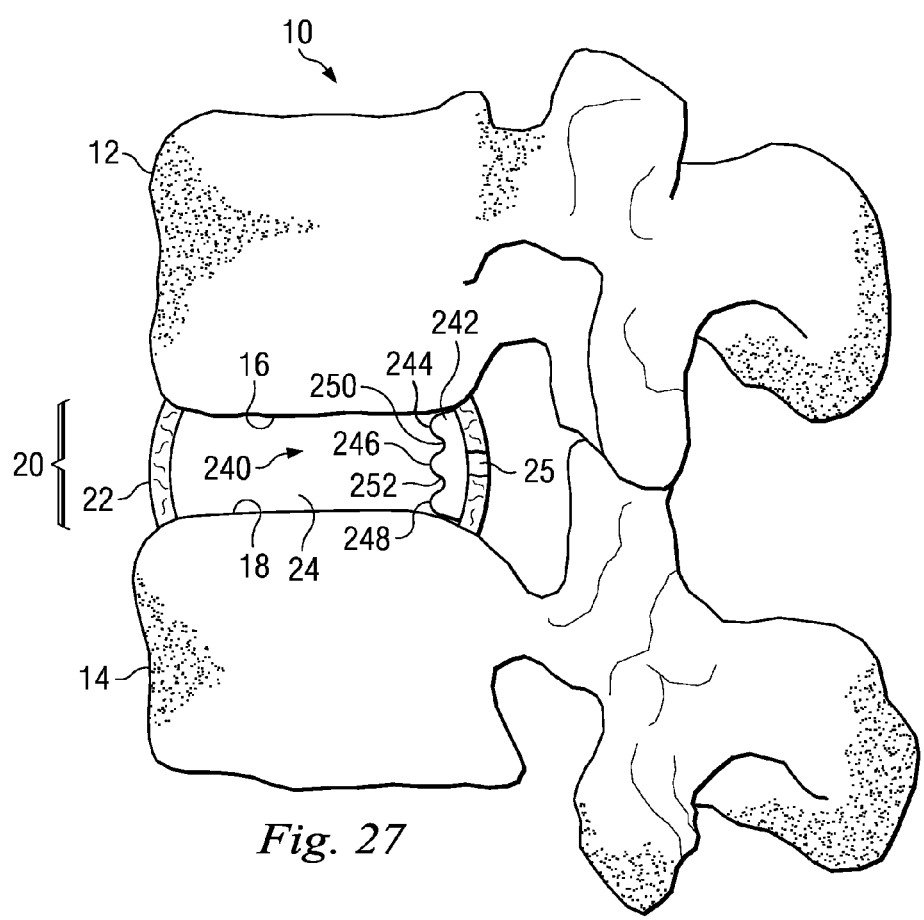
FIG. 27 is a lateral view of an expandable intervertebral treatment device disposed within an intervertebral disc according to another embodiment of the present disclosure.

Referring to FIG. 27, shown therein is a lateral view of an expandable intervertebral treatment device 240 disposed within an intervertebral disc 20 according to another embodiment of the present disclosure. The device 240 is adapted to treat a defect 25 in the annulus 22. The device 240 may be substantially similar in some aspects to the devices described above. In the current embodiment, the device 240 is an expandable device, such as a balloon, that has a predetermined expanded shape. In the present embodiment, the predetermined expanded shape includes an outer surface 242 having three convex projections 244, 246, 248 and a pair of recesses 250, 252 disposed therebetween. In the current embodiment, the projections 244, 246, 248 and the recesses 250, 252 are comprised of substantially arcuate curves. In other embodiments, the projections 244, 246, 248 and/or the recesses 250, 252 have other geometrical, arcuate, planar, and/or irregular shapes. Further, in other embodiments the device 240 includes more or less projections and/or more or less recesses.

Figure 28:
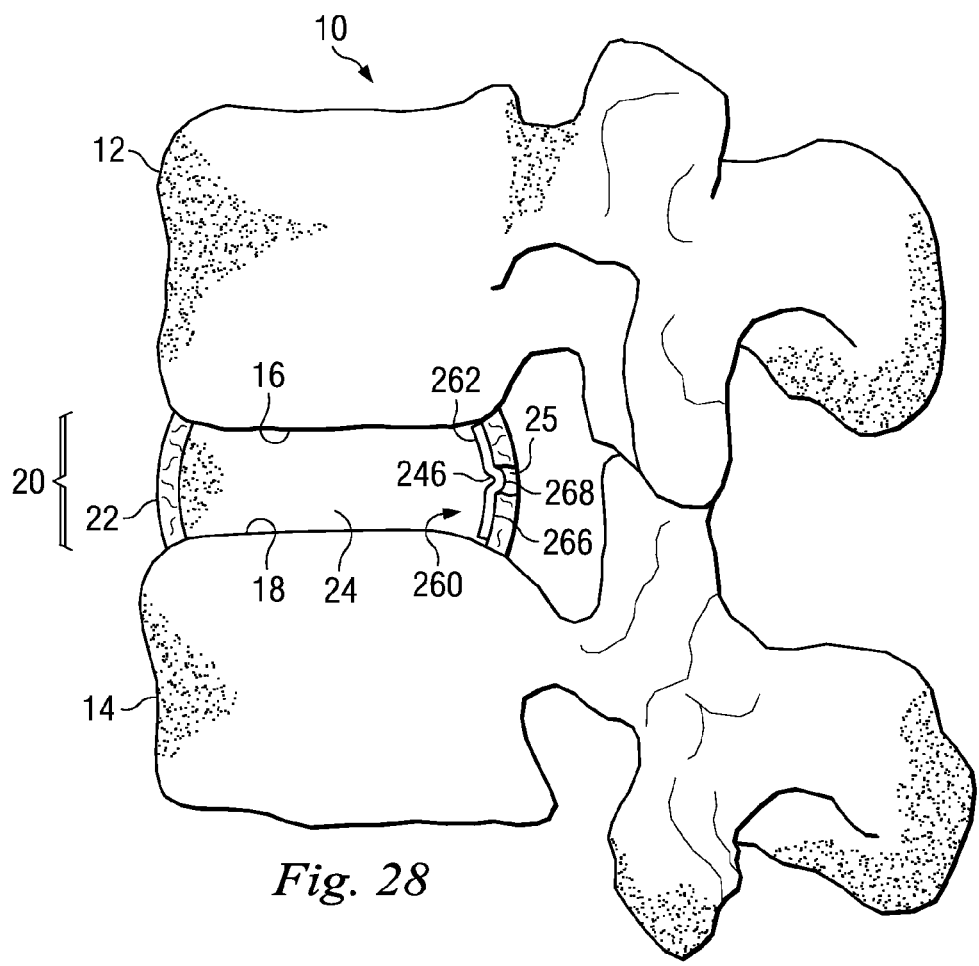
FIG. 28 is a lateral view of an expandable intervertebral treatment device disposed within an intervertebral disc according to another embodiment of the present disclosure.

Referring to FIG. 28, shown therein is a lateral view of an expandable intervertebral treatment device 260 disposed within an intervertebral disc 20 according to another embodiment of the present disclosure. The device 260 is adapted to treat a defect 25 in the annulus 22. The device 260 may be substantially similar in some aspects to the devices described above.

In the current embodiment, the device 260 is an expandable device, such as a balloon, that has a predetermined expanded shape. In the present embodiment, the predetermined expanded shape includes an outer surface 262 having a recess 264. In the current embodiment, the recess 264 is comprised of a substantially arcuate curve. In other embodiments, the recess 264 has other geometrical, arcuate, planar, and/or irregular shapes. Further, in other embodiments the outer surface 262 includes more recesses or no recesses.

The device 260 also includes an inner surface 266. The inner surface 266 includes a projection 268 extending therefrom. The projection 268 is adapted to engage with the defect 25 and/or the prepared opening in the annulus 22 to seal off the defect and/or the opening when the device 260 is positioned against the annulus 22, as shown in FIG. 28. In the current embodiment, the inner surface 266 substantially matches the contours of the outer surface 262 such that the projection 268 of the inner surface substantially aligns with the recess 264 of the outer surface. In this manner, the device 260 has a substantially constant thickness when filled with the biocompatible material. In other embodiments, the inner and outer surfaces do not have matching contours. In some embodiments, the inner surface 266 is contoured to match the inner wall of the annulus 22. Further, in the current embodiment the projection 268 is comprised of a substantially arcuate curve. In other embodiments, however, the projection 268 has other geometrical, arcuate, planar, and/or irregular shapes. Further, in some embodiments the inner surface 266 includes more projections.

While the lateral profiles and lateral cross-sectional profiles of the embodiments shown in FIGS. 25-28 are exemplary, they are by no means an exhaustive representation of various lateral profiles and/or lateral cross-sectional profiles included in the present disclosure. Rather, the expandable intervertebral treatment devices of the present disclosure may have any lateral profile and/or lateral cross-sectional profile adapted to treat a defect of an intervertebral disc. For example, but without limitation, the lateral profiles include geometrical, polygonal, symmetrical, non-symmetrical, and irregular shapes. In some embodiments, the lateral profile and/or the lateral cross-section profile is particularly shaped and/or adapted to treat a defect in the annulus of the intervertebral disc.

Figure 29:
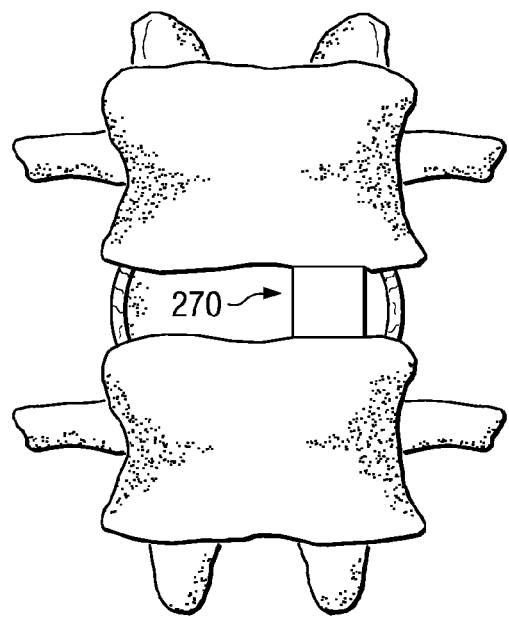
FIG. 29 is an anterior view of an expandable intervertebral treatment device disposed within an intervertebral disc according to another embodiment of the present disclosure.
Figure 30:
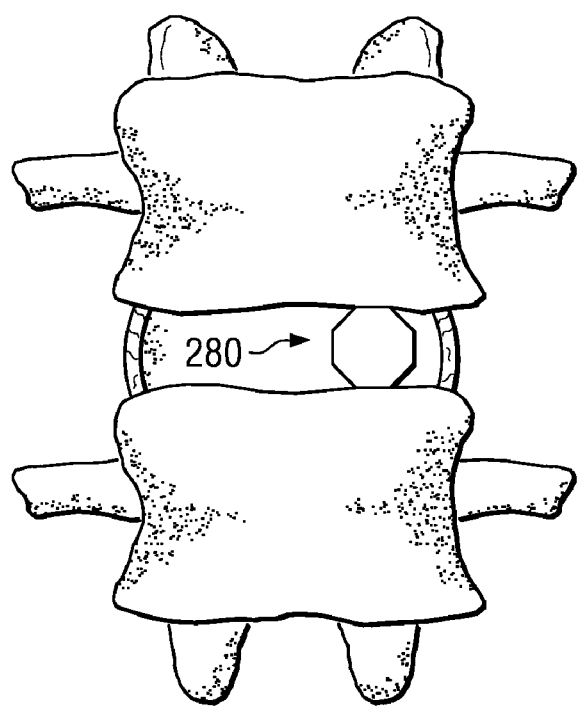
FIG. 30 is an anterior view of an expandable intervertebral treatment device disposed within an intervertebral disc according to another embodiment of the present disclosure.
Figure 31:
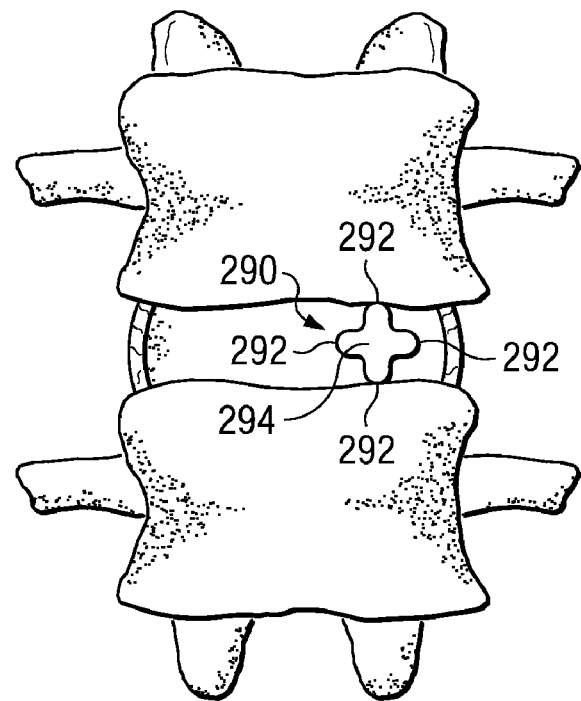
FIG. 31 is an anterior view of an expandable intervertebral treatment device disposed within an intervertebral disc according to another embodiment of the present disclosure.

Referring now to FIGS. 29-31, shown therein are alternative embodiments of an expandable intervertebral treatment device according to the present disclosure. In particular, the alternative embodiments shown in FIGS. 29-31 illustrate exemplary anterior profiles according to some aspects of the present disclosure. Referring more specifically to FIG. 29, shown therein is an anterior view of an expandable intervertebral treatment device 270 disposed within an intervertebral disc 20 according to another embodiment of the present disclosure. The device 270 has a substantially rectangular profile and, in the current embodiment, is substantially square. Referring to FIG. 30, shown therein is a lateral view of an expandable intervertebral treatment device 280 disposed within an intervertebral disc 20 according to another embodiment of the present disclosure. The device 280 has a substantially polygonal profile and, in the current embodiment, is substantially octagonal. Referring to FIG. 31, shown therein is a lateral view of an expandable intervertebral treatment device 290 disposed within an intervertebral disc 20 according to another embodiment of the present disclosure. The device 290 includes four rounded wing portions 292 extending from a central portion 294, as shown.

While the anterior profiles of the embodiments shown in FIGS. 29-31 are exemplary, they are by no means an exhaustive representation of various anterior profiles included in the present disclosure. Rather, the expandable intervertebral treatment devices of the present disclosure may have any anterior profile adapted to treat a defect of an intervertebral disc. For example, but without limitation, the anterior profiles include geometrical, polygonal, symmetrical, non-symmetrical, and irregular shapes. In some embodiments, the anterior profile is particularly shaped and/or adapted to treat a defect in the annulus of the intervertebral disc.

Figure 32:
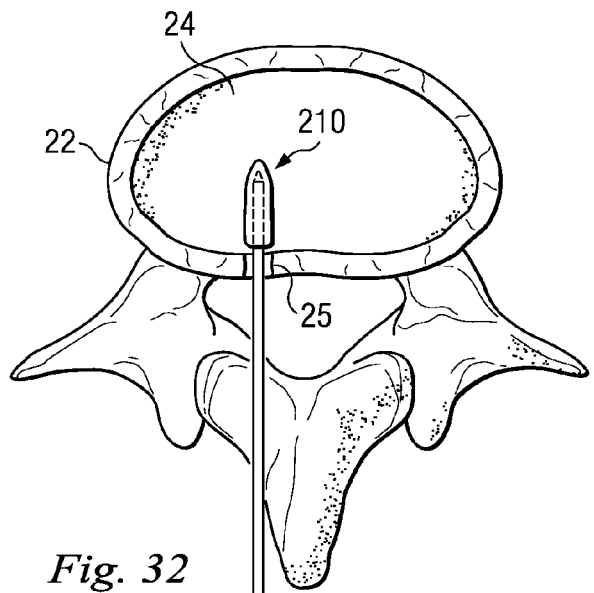
FIGS. 32-34 are lateral views of an of the implantation of the expandable intervertebral treatment device of FIG. 22.
Figure 33:
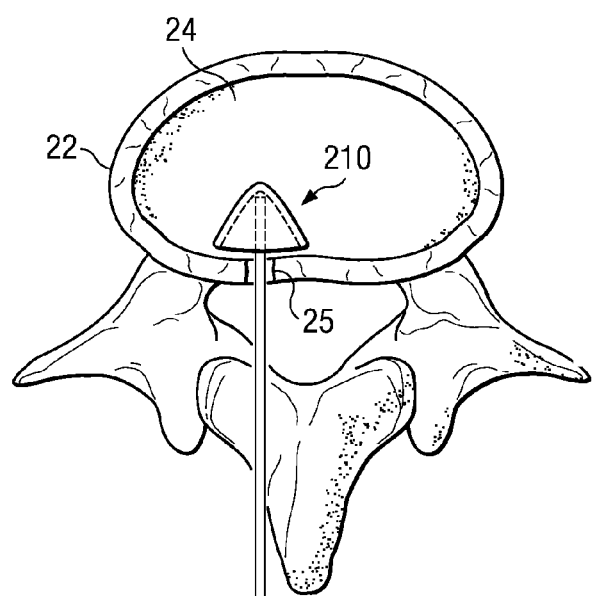
Figure 34:
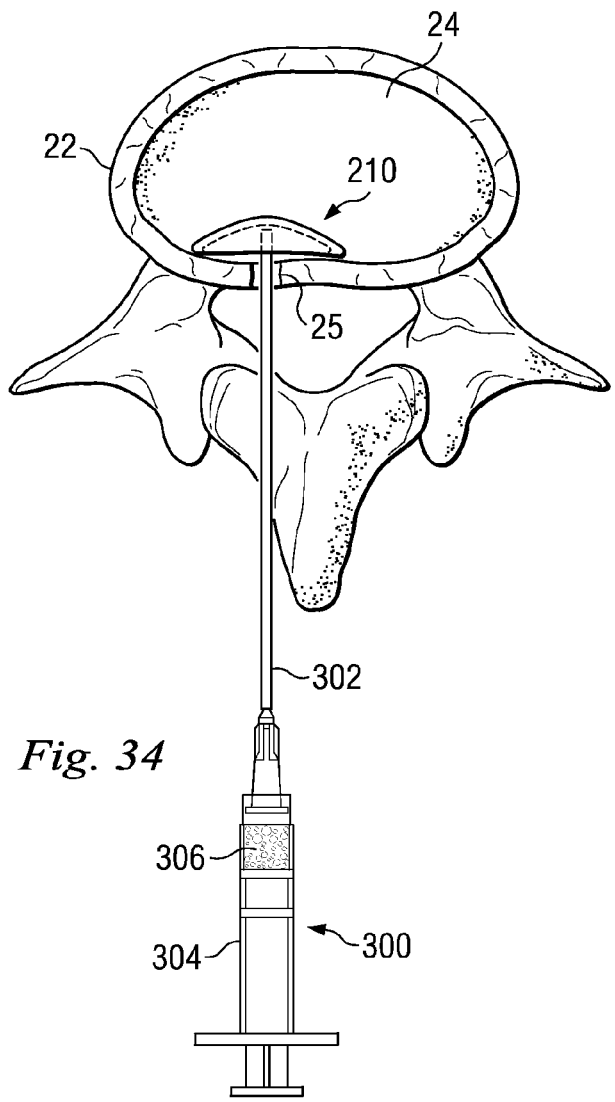

Referring now to FIG. 32-34, the expandable intervertebral treatment device 210 as shown in the embodiment of FIGS. 22-24, may, alternatively, be implanted using an implantation instrument 300 which includes a cannula portion 302 and a syringe portion 304. In the method of this surgical embodiment, the cannula 302 may be inserted into the device 210 prior to implantation. The device 210 may be collapsed around the cannula 302 and pushed through the annular defect 25, into the area of the nucleus 24 near the defect 25. In some embodiments, the collapsed device may be held in a collapsed configuration by use of a tie, elastic band, or other restraint device. Once inside the annulus 22, the device 210 may be expanded by injecting material 306, such as any of the injectable materials described above, into the device 210 to expand the device into its umbrella-like shape for occluding the defect 25. With the device 210 fully or even partially filled, the cannula 302 may be removed with the device 210 left in place to cover the defect 25.

Figure 35:
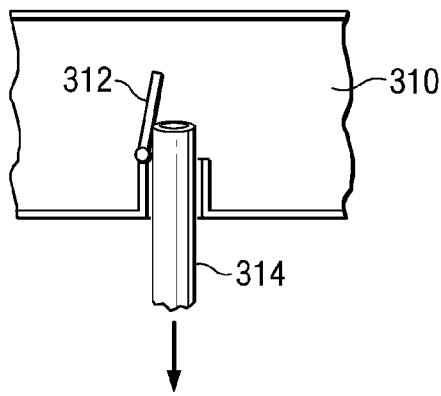
FIG. 35-36 are top views of sealing mechanisms for use with expandable intervertebral treatment devices.
Figure 36:
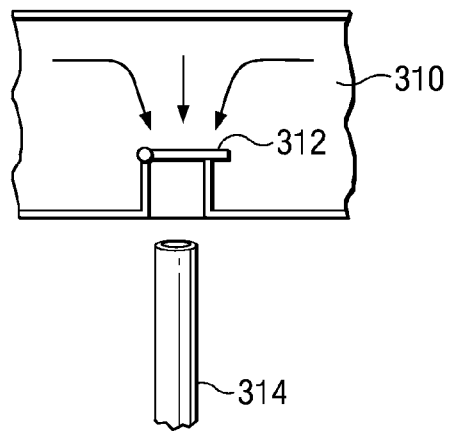

Referring now to FIGS. 35-36, although the expandable intervertebral treatment devices described above may be self sealing or sealed by the curable injected material, additionally or in an alternative surgical embodiment, a sealing system may be used. For example, an expandable intervertebral treatment device 310 which may be the same as or similar to any of those described above, may include a sealing system 312, such as a valve system to prevent injected biomaterial from escaping the filled device 310. As shown in FIG. 35, the valve 310 may be opened by an inserted cannula 314 and held open during the injection of a suitable biomaterial. When the device 310 is adequately filled, the cannula 314 may be removed with the valve 310 allowed to close to prevent leakage of the biomaterial. The pressure of the biomaterial on the valve 310, as shown in FIG. 36 may prevent the valve from reopening. The valve may be biased, such as by a spring mechanism to return the valve 310 to a closed position when the cannula 314 is removed.

Although the instruments and implants described are suitable for intervertebral applications, it is understood that the same implants and instruments may be modified for use in other regions including an interspinous region or a bone cavity. Furthermore, the instruments and implants of this disclosure may be incorporated in certain aspects into an intervertebral prosthesis device such as a motion preserving artificial disc.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," "right," "anterior," "posterior," "superior," "inferior," "upper," and "lower" are for illustrative purposes only and can be varied within the scope of the disclosure. In the claims, means-plus-function clauses are intended to cover the elements described herein as performing the recited function and not only structural equivalents, but also equivalent elements.

What is claimed is:

1. A method for treating at least one defect in an annulus of an intervertebral disc, the method comprising:
   providing an inflatable spacing device having a first deflated position and a second inflated position, wherein the spacing device is structured to have a predetermined shape in the second inflated position;
   creating a first opening in the at least one defect in the annulus to access the intervertebral disc;
   inserting the spacing device while in the deflated position through the first opening and into the nucleus pulposus of the intervertebral disc adjacent the at least one defect of the annulus in a manner such that the spacing device substantially spans the at least one defect in the annulus after being expanded to the second inflated position, wherein the spacing device substantially conforms to a portion of the annulus adjacent the defect after being expanded to the second inflated position; and has an integral projection that is expanded into the first opening when the spacing device is expanded to the second inflated position; and
   injecting a pressurized flowable biomaterial into the spacing device to inflate the spacing device from the first deflated position to the second inflated position, the inflated spacing device displacing a portion of the nucleus pulposus to create a space adjacent the defect while the spacing device expands, wherein the spacing device in the second inflated position isolates the nucleus pulposus from the annular defect, the pressurized flowable biomaterial being curable in situ;
   wherein no portion of the nucleus pulposus is removed during or subsequent to the step of creating an opening to access the intervertebral disc.

2. The method of claim 1 wherein the spacing device has a substantially convex surface and an opposing substantially concave surface in the second inflated position.

3. The method of claim 2 wherein the concave surface is positioned closer to the at least one annular defect than the convex surface.

4. The method of claim 1 wherein the spacing device has a substantially convex surface and an opposing substantially planar surface in the second inflated position.

5. The method of claim 4 wherein the planar surface is positioned adjacent the at least one annular defect.

6. The method of claim 1 further comprising:
   providing a second spacing device having a first deflated position and a second inflated position, wherein the second spacing device has a predetermined shape in the second inflated position;
   inserting the second spacing device while in the deflated position through the first opening and into the nucleus pulposus of the intervertebral disc; and injecting a pressurized flowable biomaterial into the second spacing device to expand the second spacing device from the first deflated position to the second inflated position.

7. The method of claim 1 further comprising:
providing a second spacing device having a first deflated position and a second inflated position, wherein the second spacing device has a predetermined shape in the second inflated position;
creating a second opening to access the intervertebral disc;
inserting the second spacing device while in the deflated position through the first opening and into the nucleus pulposus of the intervertebral disc adjacent a second of the at least one defect in the annulus; and
injecting a pressurized flowable biomaterial into the second spacing device to expand the second spacing device from the first deflated position to the second inflated position;
wherein the second spacing device substantially spans the second of the at least one defect in the annulus after being expanded to the second inflated position.

8. The method of claim 1 further comprising wrapping the spacing device in the first deflated position around an implantation instrument during the step of inserting.

9. The method of claim 1 further comprising placing the spacing device in the first deflated position into an implantation instrument during the step of inserting.

* * * * *